US011154592B2

(12) United States Patent
Matsuishi et al.

(10) Patent No.: US 11,154,592 B2
(45) Date of Patent: Oct. 26, 2021

(54) METHOD OF TREATING RETT SYNDROME (RTT) WITH GHRELIN

(71) Applicant: KURUME UNIVERSITY, Fukuoka (JP)

(72) Inventors: Toyojiro Matsuishi, Kurume (JP); Masayasu Kojima, Kurume (JP); Kotaro Yuge, Kurume (JP); Munetsugu Hara, Kurume (JP); Yushiro Yamashita, Kurume (JP)

(73) Assignee: KURUME UNIVERSITY, Fukuoka (JP)

( * ) Notice: Subject to any disclaimer, the term of this patent is extended or adjusted under 35 U.S.C. 154(b) by 0 days.

(21) Appl. No.: 16/437,486

(22) Filed: Jun. 11, 2019

(65) Prior Publication Data

US 2019/0307851 A1    Oct. 10, 2019

Related U.S. Application Data

(63) Continuation of application No. 15/768,101, filed as application No. PCT/JP2016/062553 on Apr. 20, 2016, now abandoned.

(30) Foreign Application Priority Data

Oct. 14, 2015    (JP) .............................. JP2015-202751

(51) Int. Cl.
*A61K 38/22* (2006.01)
*A61P 25/00* (2006.01)

(52) U.S. Cl.
CPC .............. *A61K 38/22* (2013.01); *A61P 25/00* (2018.01)

(58) Field of Classification Search
None
See application file for complete search history.

(56) References Cited

U.S. PATENT DOCUMENTS

| 7,973,049 | B2 | 7/2011 | Tung |
| 8,188,110 | B2 | 5/2012 | Tung |
| 8,440,628 | B2 | 5/2013 | Minamitake et al. |
| 8,518,893 | B2 | 8/2013 | Minamitake et al. |
| 8,541,436 | B2 | 9/2013 | Tung |
| 8,710,072 | B2 | 4/2014 | Graham et al. |
| 8,748,450 | B2 | 6/2014 | Tung |
| 8,916,582 | B2 | 12/2014 | Graham et al. |
| 9,072,711 | B2 | 7/2015 | Tung |
| 9,212,204 | B2 | 12/2015 | Glass et al. |
| 9,266,837 | B2 | 2/2016 | Graham et al. |
| 9,314,440 | B2 | 4/2016 | Tung |
| 9,340,512 | B2 | 5/2016 | Graham et al. |
| 9,655,895 | B2 | 5/2017 | Graham et al. |
| 9,708,366 | B2 | 7/2017 | Glass et al. |
| 9,868,976 | B2 | 1/2018 | Tung |
| 2006/0166871 | A1 | 7/2006 | Minamitake et al. |
| 2008/0081787 | A1 | 4/2008 | Minamitake et al. |
| 2008/0280936 | A1 | 11/2008 | Tung |
| 2009/0098421 | A1 | 4/2009 | Mills |
| 2010/0216722 | A1 | 8/2010 | Bevec et al. |
| 2010/0297115 | A1 | 11/2010 | Blaustein |
| 2011/0066414 | A1 | 3/2011 | Mills |
| 2011/0230514 | A1 | 9/2011 | Tung |
| 2011/0257214 | A1 | 10/2011 | Graham et al. |
| 2011/0306627 | A1 | 12/2011 | Tung |
| 2012/0029007 | A1 | 2/2012 | Graham et al. |
| 2012/0264691 | A1 | 10/2012 | Minamitake et al. |
| 2013/0310415 | A1 | 11/2013 | Tung |
| 2014/0113925 | A1 | 4/2014 | Tung |
| 2014/0147491 | A1 | 5/2014 | Glass et al. |
| 2014/0315940 | A1 | 10/2014 | Graham et al. |
| 2014/0329846 | A1 | 11/2014 | Tung |
| 2015/0073009 | A1 | 3/2015 | Graham et al. |
| 2015/0197543 | A1 | 7/2015 | Glass et al. |
| 2015/0336899 | A1 | 11/2015 | Graham et al. |
| 2016/0287579 | A1 | 10/2016 | Graham et al. |
| 2017/0037449 | A1 | 2/2017 | Tung |
| 2017/0281616 | A1 | 10/2017 | Graham et al. |

FOREIGN PATENT DOCUMENTS

| JP | 2010-526089 | 7/2010 |
| JP | 2011-501760 | 1/2011 |
| JP | 2012-503009 | 2/2012 |
| JP | 2012-131815 | 7/2012 |
| JP | 5000848 | 8/2012 |
| JP | 2014-508744 | 4/2014 |
| JP | 2014-196331 | 10/2014 |
| JP | 2015-145407 | 8/2015 |
| WO | 2009/040047 | 4/2009 |

OTHER PUBLICATIONS

Akamizu et al. (Eur. J. Endocrinol. 158: 491-498, 2008).*
McArthur et al., "Sleep dysfunction in Rett syndrome: atrial of exogenous melatonin treatment", Developmental Medicine & Child Neurology, 40:186-192 (1998).
Ellaway et al., "Sleep dysfunction in Rett syndrome: lack of age related decrease in sleep duration", Brain & Development, 23: S101-S103 (2001).
Nomura, "Early behavior characteristics and sleep disturbance in Rett syndrome", Brain & Development, 27:S35-S42 (2005).
Young et al., "Sleep problems in Rett syndrome", Brain & Development, 29:609-616 (2007).
Lotan et al., "The Digestive System and Nutritional Considerations for Individuals wilh Rett Syndrome", The Scientific World Journal, 6:1737-1749(2006).
Schwartzman et al., "Eating Practices, Nutritional Status And Constipation In Patients With Rett Syndrome", Arq Gastroenterol, 45(4):284-289 (2008).
Motil et al., "Gastrointestinal and Nuuitional Problems Occur Frequently Throughout Life in Girls and Women With Rett Syndrome", JPGN, 55(3):292-298 (2012).

(Continued)

*Primary Examiner* — Christine J Saoud
(74) *Attorney, Agent, or Firm* — Wenderoth, Lind & Ponack, L.L.P.

(57) ABSTRACT

A method of treating Rett Syndrome (RTT) comprising administering ghrelin to a subject in need thereof.

2 Claims, 18 Drawing Sheets

Specification includes a Sequence Listing.

(56) References Cited

OTHER PUBLICATIONS

Guy et al., "Reversal of Neurological Defects in a Mouse Model of Rett Syndrome", Science, 315:1143-1147 (2007).
Tropea et al., "Partial reversal of Rett Syndrome-like symptoms in MeCP2 mutant mice", PNAS, 106(6):2029-2034 (2009).
Marchetto et al., "A Model for Neural Development and Treatment of Rett Syndrome Using Human Induced Pluripotent Stem Cells", Cell, 143:527-539 (2010).
Deogracias et al., "Fingolimod, a sphingosine-1 phosphate receptor modulator, increases BDNF levels and improves symptoms of a mouse model of Rett syndrome", PNAS, 109(35): 14230-14235 (2012).
Derecki et al., "Wild-type microglia arrest pathology in a mouse model of Rett syndrome", Nature, 484:105-111 (2012).
Pini et al., "IGF1 as a Potential Treatment for Rett Syndrome: Safety Assessment in Six Rett Patients", Autism Research and Treatment, vol. 2012, Article ID 679801, 14 pages (2012).
Ricceri et al., "Rett syndrome treatment in mouse models: Searching for effective targets and strategies", Neuropharmacology, 68:106-115 (2013).
Ito et al., "Rett syndrome: peculiar developmental disability with autistic disorder", SRL Hokan, 34(2):28-39 (2013), with Partial English translation.
Khwaja et al., "Safety, pharmacokinetics, and preliminary assessment of efficacy of mecasermin (recombinant human IGF-1) for the treatment of Rett syndrome", PNAS, 111(12):4596-4601 (2014).
Kojima et al., "Ghrelinis a growth-hormone-releasing acylated peptide from stomach", Nature, 402:656-660 (1999).
Kojima et al., "Ghrelin: discovery of the natural endogenous ligand for the growth hormone secretagogue receptor", Trends in Endocrinology & Metabolism, 12(3):118-126 (2001)
Takaya et al., "Ghrelin Strongly Stimulates Growth Hormone (GH) Release in Humans", The Journal of Clinical Endocrinology & Metabolism 85(12):4908-4911 (2000).
Tschop et al., "Ghrelin induces adiposity in rodents", Nature, 407:908-913 (2000).
Nakazato et al., "A role for ghrelin in the central regulation of feeding", Nature, 409:194-198 (2001).
Hara et al., "Ghrelin levels are reduced in Rett syndrome patients with eating difficulties", International Journal of Developmental Neuroscience, 29:899-902 (2011).
Caffarelli et al., "The relationship between serum ghrelin and body composition with bone mineral density and QUS parameters in subjects with Rett syndrome", Bone, 50:830-835 (2012).
Hara et al., "Relation between circulating levels of Gh, IGF-1, ghrelin and somatic growth in Rett syndrome", Brain & Development, 36:794-800 (2014).
Matsuishi et al., "Rett syndrome: The state of clinical and basic research, and future perspectives", Brain & Development, 33:627-631 (2011).
Hara et al., "Relation between circulating levels of GH, IGF-1, ghrelin and somatic growth in Rett syndrome", Brain & Development, 7 pages (2013) Article in Press.
Matsuishi, "Rett syndrome: the state of research, and future perspectives", Japanese Journal of Clinical Medicine, 71(11), 11 pages (2013), with English Abstract.
Nishi et al., "A-3: Ghrelin production/secretion kinetics in Rett syndrome model mice and therapeutic application of ghrelin", Folia endocrinologica Japonica, 88(2):630, A-3 (2012), with English translation.
Matsuishi et al., "Study of ghrelin as a marker of clinical conditions of Rett syndrome and study for elucidation of disease conditions using regenerative medical techniques", General Partial Research Report for the fiscal year 2012, pp. 18-21 (2013), with Partial English translation.
Matsuishi et al., "Study of ghrelin as a marker of clinical conditions of Rett syndrome and study for elucidation of disease conditions using regenerative medical techniques", General Partial Research Report for the fiscal year 2010, pp. 23-26 (2011), with Partial English translation.
Nishi et al., "Study of production/secretion kinetics of decanoic acid-modified ghrelin cases of developmental disability or infant neurological diseases", Annual Research Report, 33:149-154 (2009), with Partial English translation.
Yuge et al., "Does ghrelin ameliorate the symptoms of Rett syndrome?—Study of development of novel therapy of Rett syndrome—", Brain & Development, 47:Supplement Scientific Meeting:S264, O-126 (2015), with English translation.
Kojima et al., "Ghrelin: Structure and Function", Physiol Rev, 85:495-522 (2005).
Garin et al., "The Human Experience with Ghrelin Administration", Journal of Climcal Endocrinology & Metabolism, 98(5): 1826-1837 (2013).
Hosoda et al., "Biological, Physiological, and Pharmacological Aspects of Ghrelin", Journal of Pharmacological Sciences, 100:398-410 (2006).
International Search Report dated June 28, 2016 in International (PCT) Application No. PCT/JP2016/062553
Written Opinion of the International Searching Authority dated Jun. 28, 2016 in International (PCT) Application No. PCT/JP2016/062553.

* cited by examiner

[Fig. 2]
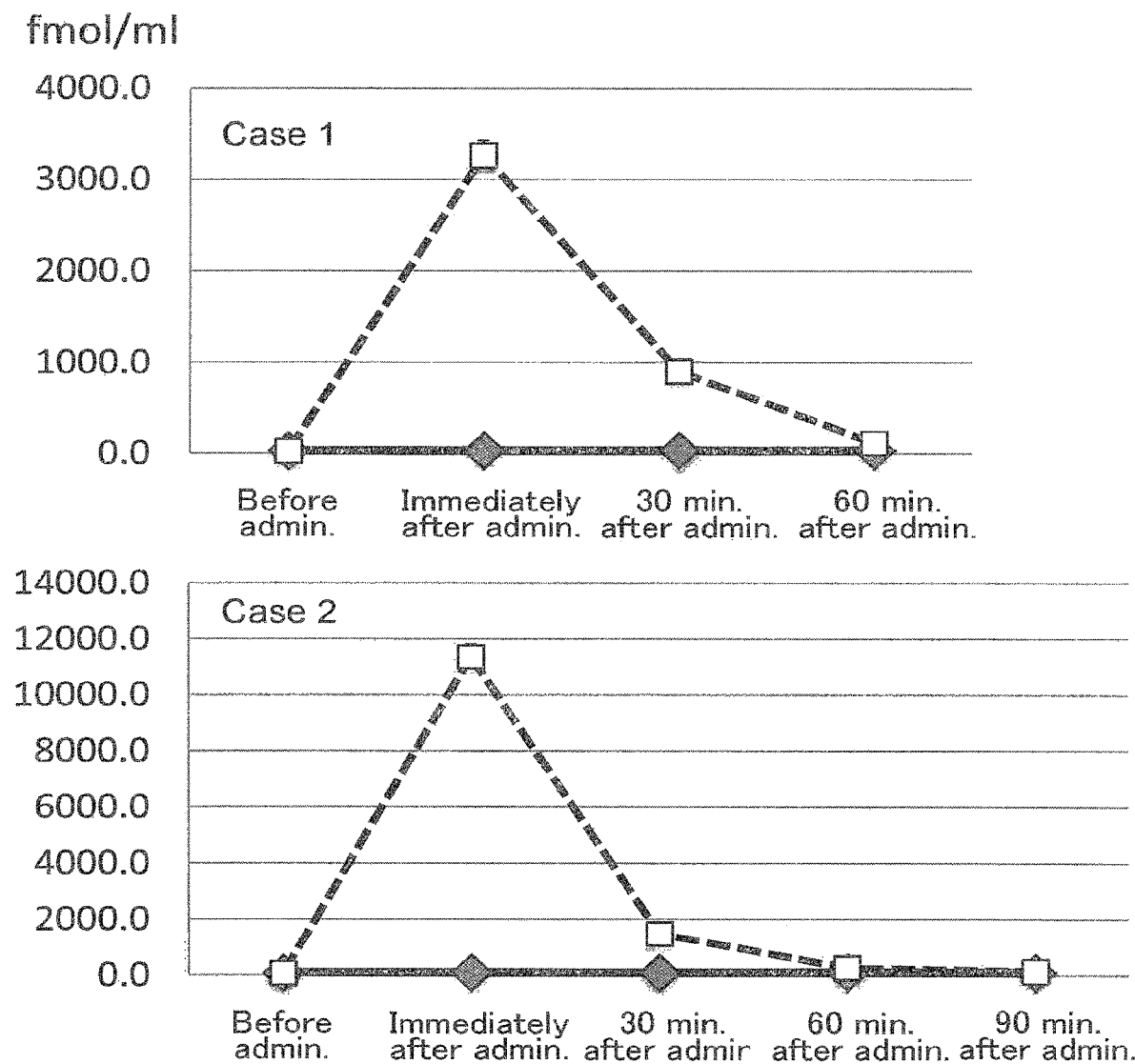

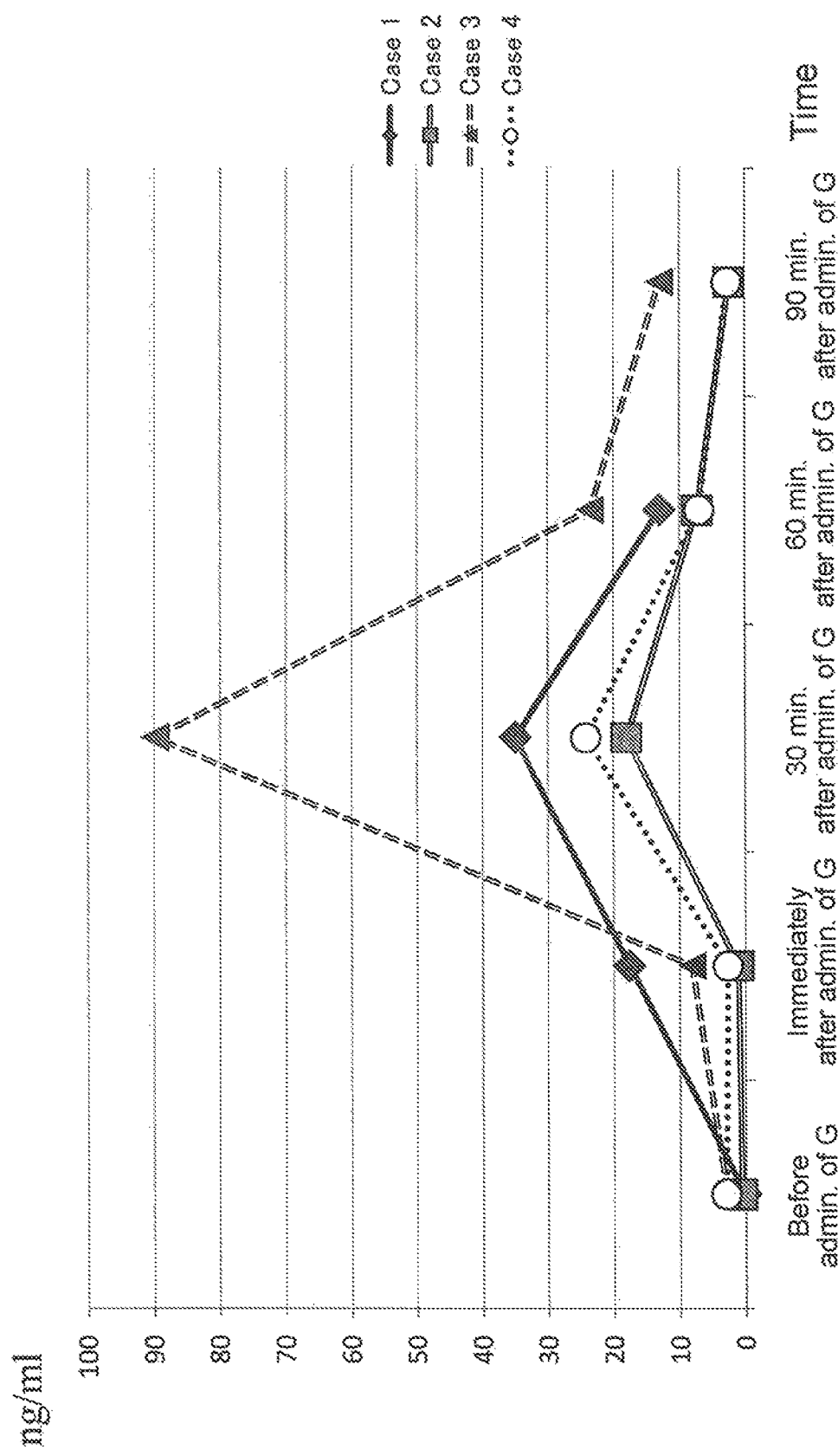

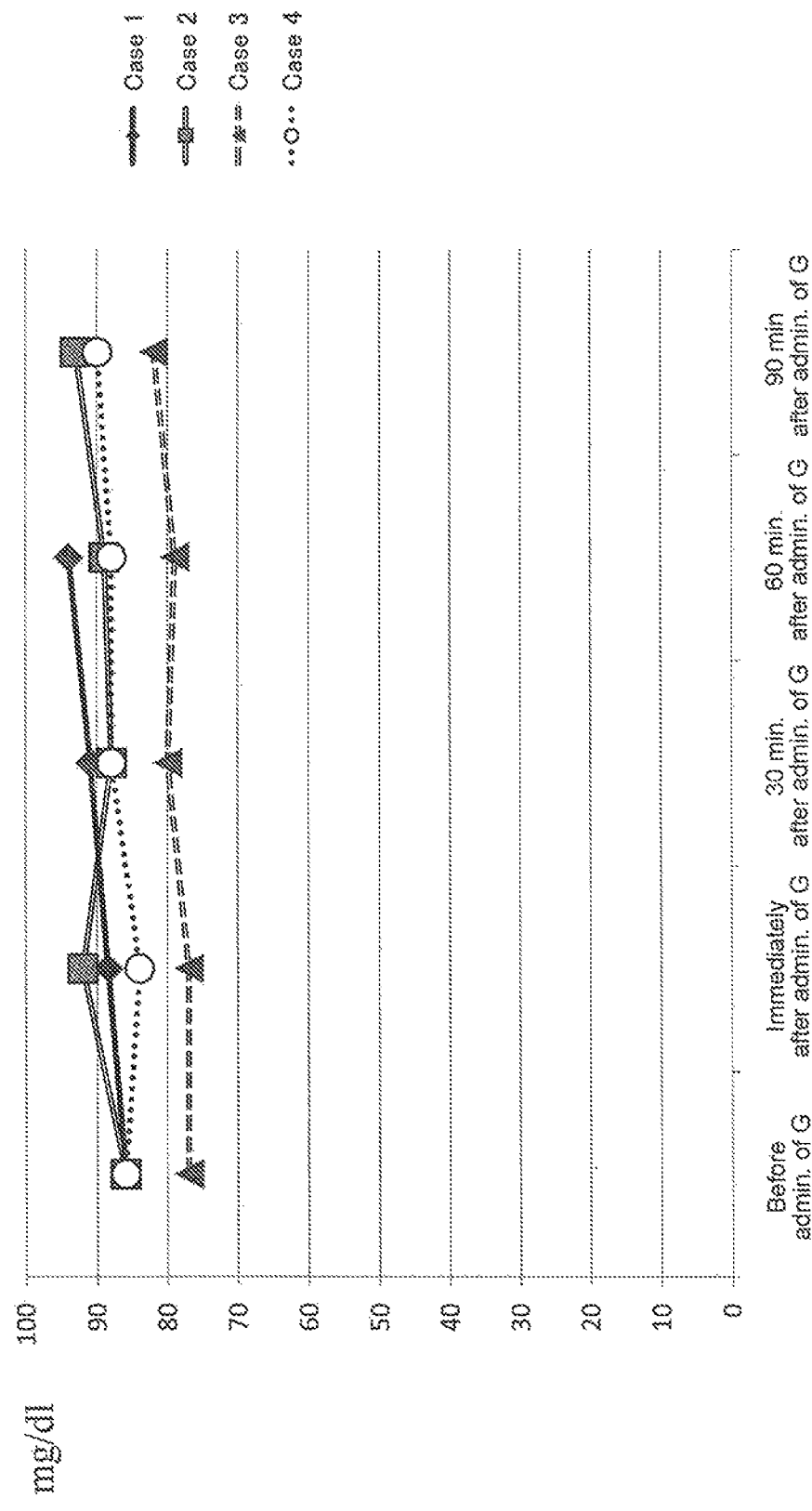
[Fig. 4]

FIG. 5C

Case 2: Surface temperature, deep body temperature

[Fig. 6]

Case 2: Steady breathing during sleep 19 times / 1 min.

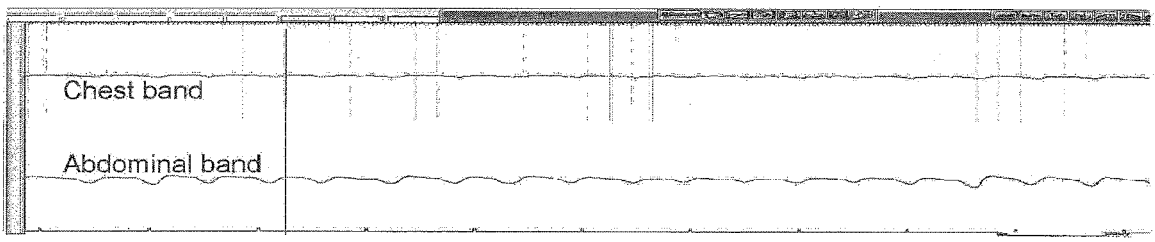

Case 2: Repeating of hyperventilation and apnea in the waking state Apnea for 28 Sec.

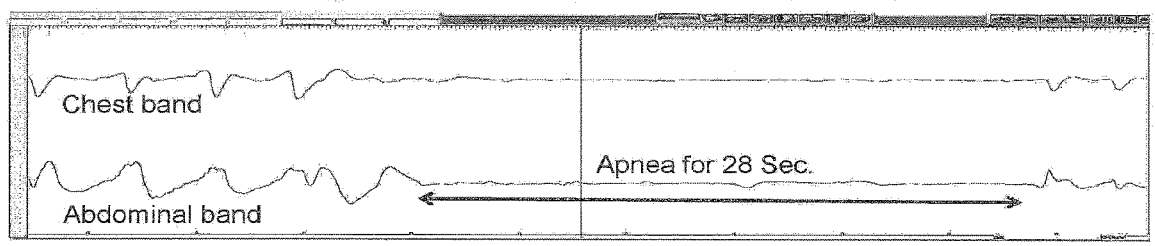

Fig. 7

| Case 2 | Before Ghrelin | After Ghrelin | Case 3 | Before Ghrelin | After Ghrelin |
|---|---|---|---|---|---|
| Times of apnea for 10 sec. or more / 30 min. | 10 times | 10 times | | 15 times | 18 times |
| Total time of apnea for 10 sec. or more / 30 min. | 180 sec | 125 sec | | 435 sec | 745 sec |
| Times of hyponea for 10 sec. or less / 30 min. | 28 times | 36 times | | 7 times | 2 times |
| Total time of hyponea for 10 Sec. or less / 30 min. | 194 sec | 230 sec | | 56 sec | 19 sec |

FIG. 8B

| | During sleep | In the waking state | As a whole |
|---|---|---|---|
| LF (ms. ms) | 321 | 291 | 300 |
| HF (ms. ms) | 63 | 73 | 70 |
| LF/HF | 5.16 | 3.97 | 4.33 |

Change of 5-min. mean value

| | LF | HF | LF/HF |
|---|---|---|---|
| 15:00.. | 338 | 60 | 5.54 |
| 16:00.. | 361 | 64 | 5.70 |
| 17:00.. | 327 | 76 | 4.38 |
| 18:00.. | 427 | 70 | 6.09 |
| 19:00.. | 294 | 57 | 5.07 |
| 20:00.. | 245 | 54 | 4.51 |
| 21:00.. | 86 | 58 | 1.55 |
| 22:00.. | 132 | 35 | 3.62 |
| 23:00.. | 82 | 36 | 2.20 |
| 0:00.. | 74 | 39 | 1.92 |
| 1:00.. | 297 | 71 | 4.30 |
| 2:00.. | 362 | 82 | 4.29 |
| 3:00.. | 377 | 78 | 4.93 |
| 4:00.. | 272 | 88 | 3.12 |
| 5:00.. | 259 | 97 | 2.70 |
| 6:00.. | 577 | 144 | 3.95 |
| 7:00.. | 460 | 129 | 3.65 |
| 8:00.. | 704 | 104 | 7.24 |
| 9:00.. | 551 | 78 | 7.51 |
| 10:00.. | 149 | 28 | 5.24 |
| 11:00.. | 129 | 41 | 4.12 |
| 12:00.. | 107 | 66 | 1.67 |
| 13:00.. | 445 | 99 | 4.39 |
| 14:00.. | 179 | 34 | 5.59 |
| 15:00.. | 229 | 31 | 7.34 |
| 16:00 | | | |

Name of data file / Name of subject / Subject ID
beatinfo1.CSV
nakanonatumi
—

Measurement was started at 2014-07-30 14:51:56

< LF – Circadian rhythm curve >

| Maximum value | 8:07 | 561 |
|---|---|---|
| Minimum value | 22:42 | 24 |
| Highest increase rate (/hour) | 0:27 | 145 |
| Lowest decrease rate (/hour) | 10:07 | −177 |
| Level | | 301 |

| Period | Amplitude | Power ratio (%) | |
|---|---|---|---|
| 15.6 | 160 | 25.4 | 25.4 |
| 6.5 | 120 | 14.6 | 40.0 |

< HF – Circadian rhythm curve >

| Maximum value | 7:17 | 140 |
|---|---|---|
| Minimum value | 10:42 | 31 |
| Highest increase rate (/hour) | 5:57 | 30.8 |
| Lowest decrease rate (/hour) | 8:57 | −51.5 |
| Level | | 72.9 |

| Period | Amplitude | Power ratio (%) | |
|---|---|---|---|
| 17.8 | 28.9 | 32.8 | 32.8 |
| 10.6 | 15.4 | 9.1 | 41.9 |
| 6.1 | 16.3 | 10.8 | 52.7 |
| 5.1 | 15.6 | 9.9 | 62.6 |

< LF/HF – Circadian rhythm curve >

| Maximum value | 9:12 | 7.60 |
|---|---|---|
| Minimum value | 23:37 | 2.32 |
| Highest increase rate (/hour) | 7:37 | 2.44 |
| Lowest decrease rate (/hour) | 10:47 | −2.45 |
| Level | | 4.136 |

| Period | Amplitude | Power ratio (%) | |
|---|---|---|---|
| 18.1 | 1.176 | 11.4 | 11.4 |
| 7.0 | 1.486 | 18.5 | 29.9 |
| 5.5 | 0.850 | 6.2 | 36.2 |

[Fig. 9]
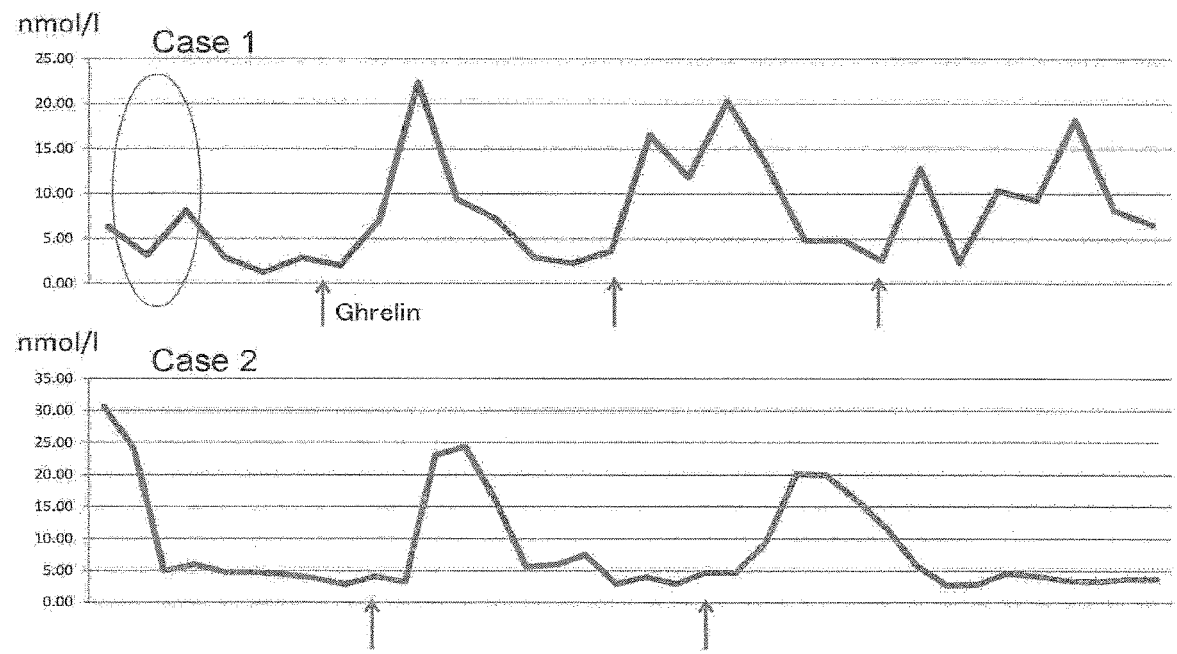
Fig. 10
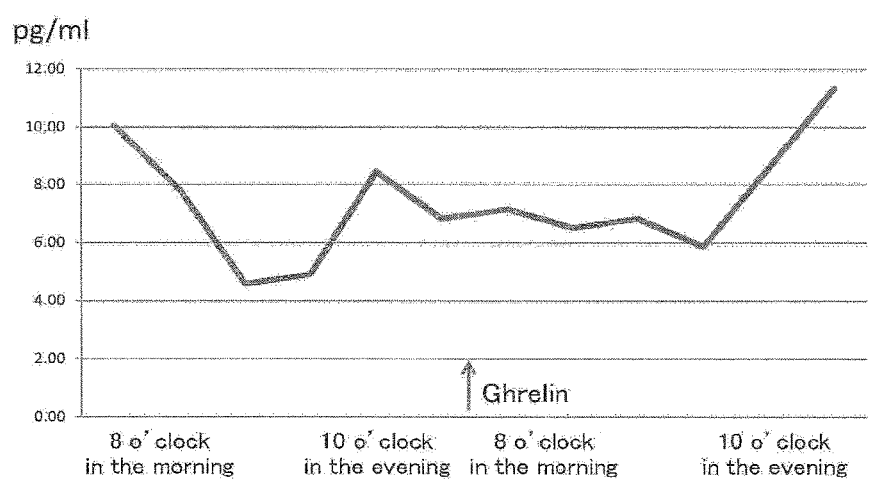

[Fig. 11]
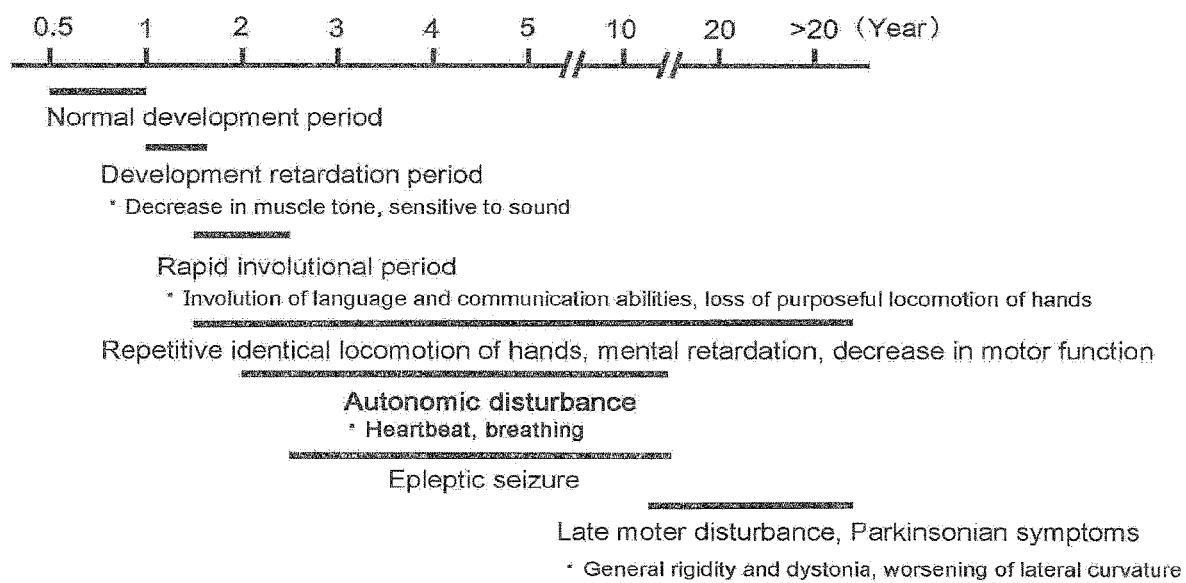

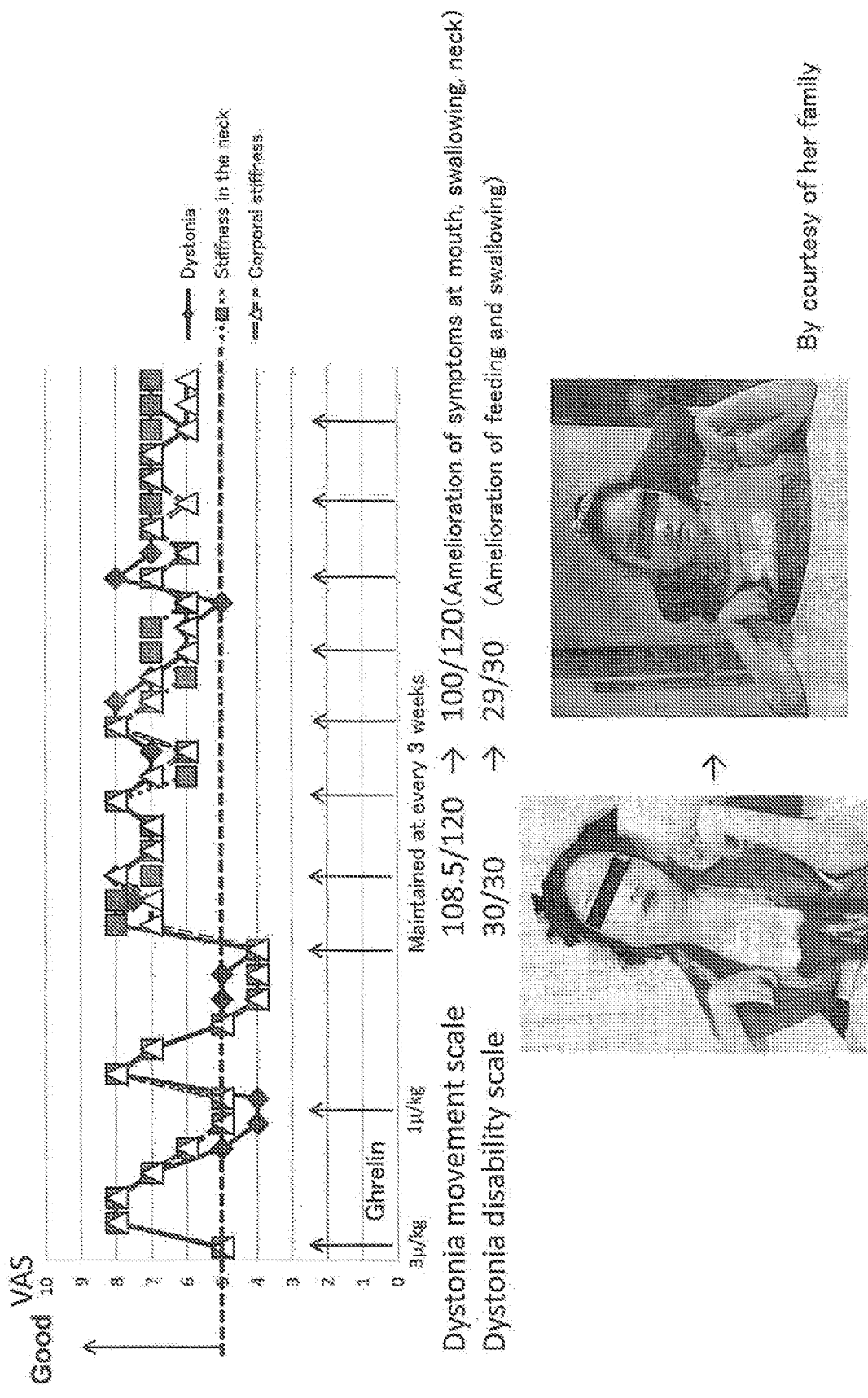
[Fig. 13]

METHOD OF TREATING RETT SYNDROME (RTT) WITH GHRELIN

TECHNICAL FIELD

The present invention relates to a novel use of ghrelin in the clinical field. Specifically, the present invention relates to a prophylactic and therapeutic agent for Rett Syndrome (RTT) comprising ghrelin as an active ingredient.

Rett Syndrome (RTT) is a neurodevelopmental disorder which begins during infancy, characterized by intellectual disability, autistic behavior, epilepsy, etc. with various other symptoms such as autonomic dysfunction, gastrointestinal and respiratory problems. RTT was first described by Austrian pediatric neurologist Andreas Rett in 1966. It received global attention after a report by the Swedish Bengt Hagberg et al. in 1983. The prevalence of RTT is estimated to be 0.9 per 10,000 in females before adulthood in Japan. An estimate in Japan is that there are at least 1,000 patients with RTT but actual number of patients is thought to be more. As RTT occurs almost exclusively in females, it was proposed as caused by an X-linked dominant mutation. Exclusion mapping studies mapped the locus to Xq28 on the long arm of the X chromosome in 1996. In 1999, a causative gene mutation was discovered in methyl-CpG binding protein 2 (MECP2) (MECP2 gene).

RTT develops mainly in female infants, who exhibit hypotonia and autistic tendencies in early infancy and then impaired locomotion, such as crawling and walking, retardation of language development and, finally, severe intellectual disabilities. From infancy to early childhood, there is a loss of purposeful motor functions of the hand, such as in hand washing, kneading, handwringing or bringing one hand to the mouth while pounding on the chest, with distinctive hand stereotypies. These symptoms are almost always present in typical RTT cases. Among other clinical manifestations of RTT are stagnated head circumference development and acquired microcephaly, early childhood hypertonia, dystonia, grinding of the teeth, respiratory abnormalities such as hyperventilation and apnea, constipation, autonomic nervous dysfunctions, such as in cold sensation, small feet and frequent occurrences of epilepsy. However, these symptoms are not always present as essential criteria. An important aspect of the disease is that the symptoms occur in an age-dependent manner. In 1999, Amir et al. found that a mutation in the methyl-CpG-binding protein 2 gene (MECP2 gene) was causative in RTT. It was reported that the MECP2 gene mutation was identified in 90% or more of typical cases. In some cases, psychomotor function is ameliorated at certain clinical stages and a pseudo-stable is observed. RTT is understood to be neurodevelopmental, rather than a neurodegenerative, disorder. Angela J McArthur et al., Developmentulhledicitie & Cbild Neirrology 1998, 40, 186-192 (Non-patent reference 1); Carolyn Ellaway et al., Brain & Development 23 (2001) S101-S103 (Non-patent reference 2); Yoshiko Nomura, Brain & Development 27 (2005) S35-S42 (Non-patent reference 3); Deidra Young et al., Brain & Development 29 (2007) 609-616 (Non-patent reference 4); Meir Lotan et al., The Scientific World Journal (2006) 6, 1737-1749 (Non-patent reference 5); Flavia Schwartzman et al., Arq Gastroenterol v. 45, no. 4, July set. 2008 (Non-patent reference 6); Kathleen J. Motil et al., JPGN Volume 55, Number 3, September 2012 (Non-patent reference 7).

Uniform diagnostic criteria for RTT were not established until recently. It is important that diagnostic criteria for typical RTT of female infant meet all of the following, consisting of essential requirements and exclusion criteria for typical RTT.

Essential Requirements:
(1) Partial or complete loss of acquired purposeful hand skills
(2) Partial or complete loss of acquired spoken language
(3) Gait abnormalities: impaired (dyspraxic) or absent abilities
(4) Stereotypic hand movements Exclusion criteria for typical RTT:
Brain injury secondary to trauma (perinatally or postnatally), neurometabolic diseases or severe infection causing neurological problems, grossly abnormal psychomotor development in the first six months of life For RTT, there is not yet an established effective therapy. Jacky Guy et al. reported that about 70% of the symptoms of RTT were partially reversed in a conditional knockout mouse when conditioning knockout mouse model of the causative gene MECP2 of Rett Syndrome was prepared and administered with tamoxifen (TM) at 3-4 weeks and 12-17 weeks, at which the symptoms of Rett Syndrome occur, so as to let the MECP2 be expressed (SCIENCE VOL 315 23 Feb. 2007 (Non-patent reference 8)).

Daniela Tropea et al. reported the results of Phase I study where extended lifespan, improved locomotor function, and amelioration in respiratory and cardiac function were observed when Rett Syndrome model mice were administered with IGF-1 (PNAS Feb. 10, 2009 vol. 106, no. 6, 2029-2034 (Non-patent reference 9)).

Maria C. N. Marchetto et al. described iPS cells established from fibroblasts harvested from patients with RTT. After extensive study, they found that iPS cells from patients with RTT had fewer synapses, lower neurite densities, smaller cell sizes, altered calcium signaling and electrophysiological defects (Cell 143, 527-539, Nov. 12, 2010 (Non-patent reference 10)). Therapeutic candidates were studied by treating the iPS cells with various agents and it was shown that IGF-1 treatment led to neurite elongation, suggesting a potential therapeutic approach.

Ruben Deogracias et al. reported that fingolimod, a modifier of the sphingosine-1 phosphate receptor, increased (BDNF) levels and ameliorated symptoms in RTT model mice (PNAS Aug. 28, 2012 vol. 109 no. 35, 14230-14235 (Non-patent reference 11)).

Noel C. Derecki et al. reported that wild microglia cells, when bone-marrow was transplanted to mouse model animal, could increase lifespan, ameliorate respiratory disorder, decrease apnea, ameliorate weight gain and locomotion activity, close to those of wild mice (Nature Vol 4844, 5 Apr. 2012, 105-111 (Non-patent reference 12)).

Giorgio Pini et al. reported that IGF-1 was administered to six patients with RTT, ages 4-11 years. The IGF-1 was administered twice per day for 6 months at 0.05 mg/kg. The International Severity Score was ameliorated in three patients, the test could be performed safely and drug tolerability was confirmed (Autism Research and Treatment, Volume 2012, Article ID 679801, 14 pages (Non-patent reference 13)).

Laura Ricceri et al. reviewed clinical and neurobiological aspects of RTT and then discussed clinical therapeutic candidates targeting GABA, neurotoxin-related material, NMDA receptor, acetylcholine, biogenic amines, neurotrophic factors including BDNF, IGF1 and carnitine, corticosterone and stress coping, RhoGTPase and glial cells (Neuropharmacology 68 (2013) 106-115 (Non-patent reference 14)).

Ito M et al. reviewed recent clinical trials in RTT, evaluating IGF-1, the tricyclic antidepressant desipramine, antitussive dextromethorphan (inhibiting activity against non-selective reuptake of serotonin and an NMDA-type glutamate receptor inhibitor), bone marrow transplantation and fingolimod, which increases BDNF expression (SRL Hokan, Vol. 34, No. 2, 2013 28-39 (Non-patent reference 15));

Omar S. Khwaja et al. reported that recombinant human IGF-1, mecasermin, was administered to 9 patients with RTT at 40 to 120 µg/kg twice daily. The investigators analyzed subjects based on cerebrospinal fluid samples, electroencephalogram, cardiac function and respiration. The results showed that IGF-1, known not to cross the blood-brain barrier, could be administered safely. However, they observed increased IGF-1 levels in cerebrospinal fluid. Anxiety and mood improvements were indicated by the reversal of right frontal band asymmetry of the alpha wave of EEGs. However, the subsequent phase II trial failed to show significant difference (PNAS Mar. 25, 2014 vol. 111, no. 12, 4596-4601 (Non-patent reference 16)).

Previous trials for RTT, to date, tested a morphinan compound (JP 2010-526089 (Patent reference 1), JP 2012-131815 (Patent reference 2), JP 2012-503009 (Patent reference 3), JP 2014-196331 (Patent reference 4), JP 2015-145407 (Patent reference 5)), glycyl-L-2-methylpropyl-L-glutamic acid (JP 2014-508744 (Patent reference 6)) and a tyrosine kinase receptor B (TrkB) binding molecule (JP 2011-501760 (Patent reference 7)).

Although various trials for treating human RTT have been performed, no effective therapy has yet been established. Gene therapy and bone marrow transplantation ameliorated symptoms and increased lifespan in an animal model of RTT. However, these approaches were considered to be potentially difficult for treating human RTT. IGF-1 showed no side effects but no significant efficacy was observed. BDNF (brain derived neurotrophic factor), glutamate receptor antagonists, antidepressants and other drug classes are potential candidates for clinical trials in RTT, with some trials already underway (in the United States and Europe) (Non-patent reference 17).

Ghrelin is a peptide hormone first detected in the stomach as an endogenous ligand of GHS receptor, an orphan receptor without known ligand (Kojima M et al., Nature 402, 656-660 (1999) (Non-patent reference 18); Kojima M et al., Trends Endocrinol Metab 12, 118-122 (2001) (Non-patent reference 19). Human ghrelin is a 28 amino acid peptide in which the side chain of the 3rd amino acid residue, serine, is modified with the fatty acid octanoic acid (N-GSSFL-SPEHQRVQQRKESKKPPAKLQPR-C (SEQ ID NO:1)). This octanoic acid modification is essential for its biological activity. Namely, ghrelin is transformed into an active form by octanoylation to exhibit its physiologic activities. Ghrelin was identified in fish, amphibian, birds and many mammalian species and has a fatty acid at the 3rd serine or threonine residue. It is a peptide hormone with potent growth hormone secretion promoting and feeding stimulating activities which regulates endocrine and energy metabolism (Takaya K et al., J Clin Endocrinol Metab 85, 4908 (2000) (Non-patent reference 20); Tschop M et al., Nature 407, 908 (2000) (Non-patent reference 21); Nakazato M et al., Nature 409, 194 (2001) (Non-patent reference 22)).

The ghrelin producing cells in the stomach are called X/A-like cells, function of which is not known up till the present. Besides in the stomach, production of ghrelin, though in lesser amounts, is observed in tissues including the intestinal tract, hypothalamus, pituitary gland, pancreas, kidney, placenta and testes. Plasma ghrelin levels increase with fasting and decrease with food intake. Plasma ghrelin levels are lower in obese individuals and higher under lean conditions. Ghrelin acts in the pituitary gland to stimulate GH secretion. This activity is synergistic with that of growth hormone-releasing hormone (GHRH). Ghrelin also acts in the hypothalamus to stimulate food intake and, thus, acts as a feeding promoting peptide. Weight gain and increased adipose tissue is observed after ghrelin administration. Therefore, ghrelin is considered to be a hormone antagonistic to leptin, an anti-obesity hormone produced in fat cells.

As described above, ghrelin is mainly produced in gastric endocrine cells and has an important activity in regulating energy metabolism such as feeding promotion, weight gain and regulation of gastrointestinal function. It is, so far, the only peptide hormone produced in the periphery with feeding promoting activity. Ghrelin is secreted in the stomach when hunger signals are transmitted to the brain via the afferent vagus nerve. Ghrelin acts in the hypothalamus, which is the central region for regulating feeding and GH secretion.

Ghrelin is present in the α cells which produce glucagon in the pancreatic islets. The ghrelin receptor gene is expressed in both α and β cells. Ghrelin at physiological concentrations ($10^{-12}$ to $10^{-11}$ M) increases intracellular $Ca^{2+}$ levels in pancreatic β cells isolated from rats under hyperglycemic conditions, promoting insulin secretion. On the other hand, under hypoglycemic conditions, ghrelin does not affect intracellular $Ca^{2+}$ levels or insulin secretion in pancreatic β cells. Another possible effect is that ghrelin modifies insulin activity in the liver and is involved in glucose metabolism. Ghrelin, when intravenously administered to healthy subjects, decreases average arterial blood pressure without changing heart rate and increases cardiac output. When ghrelin is continually administered in a rat model for heart failure after cardiac infarction, ghrelin levels are increased in the left ventricular ejection fraction together with an increase in serum GH and alleviation of cachexia. These observations suggested the usefulness of ghrelin as a drug to treat heart failure because of its amelioration of cardiac dysfunction and malnutrition. Furthermore, when ghrelin was administered to patients with chronic heart failure, increased cardiac index and improved hemodynamics were reported.

Munetsugu Hara et al. measured plasma ghrelin levels in 27 patients with RTT and 53 healthy controls. The plasma levels of both total ghrelin and active ghrelin with octanoyl modification were lower in patients with RTT than in healthy controls (Int. J. Devl Neuroscience 29 (2011) 899-902 (Non-patent reference 23)). In addition, plasma levels of total ghrelin were positively correlated with serum IGF-1 levels and head circumference. There was also a correlation between decreased plasma levels of total and active ghrelin and eating difficulties and constipation, as well as between decreased plasma levels of active ghrelin and eating difficulties.

C. Caffarelli et al. reported comparison between 123 female RTT patients and 55 healthy controls in Italy (Bone 50 (2012) 830-835 (Non-patent reference 24)). In a study of ghrelin and bone density, adolescent patients with RTT had higher ghrelin levels, lower total bone densities and a lower total bone mineral content/height ratio. In adolescent female patients with RTT, serum ghrelin levels were inversely correlated with bone age and BMI.

Munetsugu Hara et al. reported comparison between plasma levels of ghrelin, GH and IGF-1 with anthropometric data (weight, height, BMI and head circumference) in 22 patients with RTT, associated with MECP2 gene mutations, and 14 age- and gender-matched healthy controls (Brain & Development 36 (2014) 794-800 (Non-patent reference 25)). To subdivide the patients with (RTT) and without (non-RTT) MeCP2 mutations in the group with epilepsy and intellectual disabilities, those with RTT had significantly lower BMI values and heights than those in the non-RTT group. More significantly, there was an inverse correlation between plasma ghrelin levels and head circumference in the RTT group.

Toyojiro Matsuishi et al. reviewed an interim report that plasma levels of total ghrelin were lower in patients with RTT than in healthy controls. This suggested that ghrelin plays an important role in the pathophysiology of RTT (Brain & Development 33 (2011) 627-631 (Non-patent reference 26)).

Toyojiro Matsuishi reviewed the discovery of RTT, discovery of its causative gene, establishment of an animal model and current therapeutic candidates identified using model animals and presented therapeutic agents and future perspectives animals or human (Japanese Journal of Clinical Medicine, Vol. 71, No. 11 (2013) 2043-2053) (Non-patent reference 27)).

To date, there have only been a few studies on ghrelin and RTT. However, there remains a lack of understanding and the potential use of ghrelin as therapeutic agent for RTT was not known.

PRIOR ART

Patent Reference

Patent reference 1: JP 2010-526089
Patent reference 2: JP 2012-131815
Patent reference 3: JP 2012-503009
Patent reference 4: JP 2014-196331
Patent reference 5: JP 2015-145407
Patent reference 6: JP 2014-508744
Patent reference 7: JP 2011-501760

Non-Patent Reference

Non-patent reference 1: Angela J McArthur et al., Developmentulhledicitie & Cbild Neirrology (1998) 40, 186-192
Non-patent reference 2: Carolyn Ellaway et al., Brain & Development (2001) 23, S101-S103
Non-patent reference 3: Yoshiko Nomura, Brain & Development (2005) 27, S35-S42
Non-patent reference 4: Deidra Young et al., Brain & Development (2007) 29, 609-616
Non-patent reference 5: Meir Lotan et al., The Scientific World JOURNAL (2006) 6, 1737-1749
Non-patent reference 6: Flavia Schwartzman et al., Arq Gastroenterol (2008) v. 45, no. 4, July set.
Non-patent reference 7: Kathleen J. Motil et al., JPGN (2012) Volume 55, Number 3, September
Non-patent reference 8: Jacky Guy et al., SCIENCE (2007) 315, 23 FEBRUARY
Non-patent reference 9: Daniela Tropea et al., PNAS (2009) February 10, 106, no. 6, 2029-2034
Non-patent reference 10: Maria C. N. Marchetto et al., Cell (2010) November 12, 143, 527-539
Non-patent reference 11: Rube'n Deogracias et al., PNAS (2012) August 28, 109, no. 35, 14230-14235
Non-patent reference 12: Noel C. Derecki et al., Nature (2012) 5 April, 484, 105-111
Non-patent reference 13: Giorgio Pini et al., Autism Research and Treatment (2012), 2012, Article ID 679801, 14 pages
Non-patent reference 14: Laura Ricceri et al., Neuropharmacology (2013) 68, 106-115
Non-patent reference 15: Ito et al., SRL Hokan (2013) 34, No. 2
Non-patent reference 16: Omar S. Khwaja et al., PNAS (2014) March 25, 111, no. 12, 4596-4601
Non-patent reference 17: Kojima M et al., Nature (1999) 402, 656
Non-patent reference 18: Kojima M et al., Trends Endocrinol Metab (2001)12, 118
Non-patent reference 19: Takaya K et al., J Clin Endocrinol Metab (2000)85, 4908
Non-patent reference 20: Tschop M et al., Nature (2000)407, 908
Non-patent reference 21: Nakazato M et al., Nature (2001) 409, 194
Non-patent reference 22: Munetsugu Hara et al., Int. J. Devl Neuroscience (2011) 29, 899-902
Non-patent reference 23: C. Caffarelli et al., Bone (2012) 50, 830-835
Non-patent reference 24: Munetsugu Hara et al., Brain & Development (2014) 36, 794-800
Non-patent reference 25: Toyojiro Matsuishi et al., Brain & Development (2011) 33, 627-631
Non-patent reference 26: Munetsugu Hara et al., Brain & Development (2013) article in press
Non-patent reference 27: Toyojiro Matsuishi, Japanese Journal of Clinical Medicine, (2013-11) 71, No. 11, 2043-2053

DISCLOSURE OF THE INVENTION

Technical Problem to be Solved by the Invention

Until now, no effective therapeutic methods for RTT were established. RTT is a neurodevelopmental disorder with various symptoms such as neurological symptoms including dystonia, seizures, sleep disturbances, eating disorders and emaciation. A therapeutic agent for ameliorating these symptoms is needed.

Means for Solving the Problem

The present inventors conducted research to identify an effective therapeutic method for RTT. As a result, they found that ghrelin levels decreased in patients with RTT in an age-dependent manner and were correlated with gastrointestinal symptoms such as feeding and constipation, and autonomic nervous symptoms, thereby completing the present invention.

Thus, the present invention relates to pharmaceutical composition comprising ghrelin and a pharmaceutically acceptable carrier. In particular, the present invention relates to a prophylactic and therapeutic agent for RTT comprising a therapeutically effective amount of ghrelin. In accordance with the present invention, ghrelin was actually administered to patients with RTT to prove its effectiveness.

Effects of the Invention

The prophylactic and therapeutic agent for RTT of the present invention comprising a therapeutically effective amount of ghrelin can be administered to patients safely without severe side effects and exerts the effects of increased GH secretion and amelioration of constipation, sleep, muscle tone and dystonia.

BRIEF DESCRIPTION OF DRAWINGS

FIG. 2 shows changes in plasma ghrelin levels with the passage of time in patients with RTT after administration of ghrelin.

FIG. 3 shows changes in growth hormone secretion with the passage of time in patients with RTT after administration of ghrelin.

FIG. 4 shows changes in blood glucose with the passage of time in patients with RTT after administration of ghrelin.

Figure 5C:
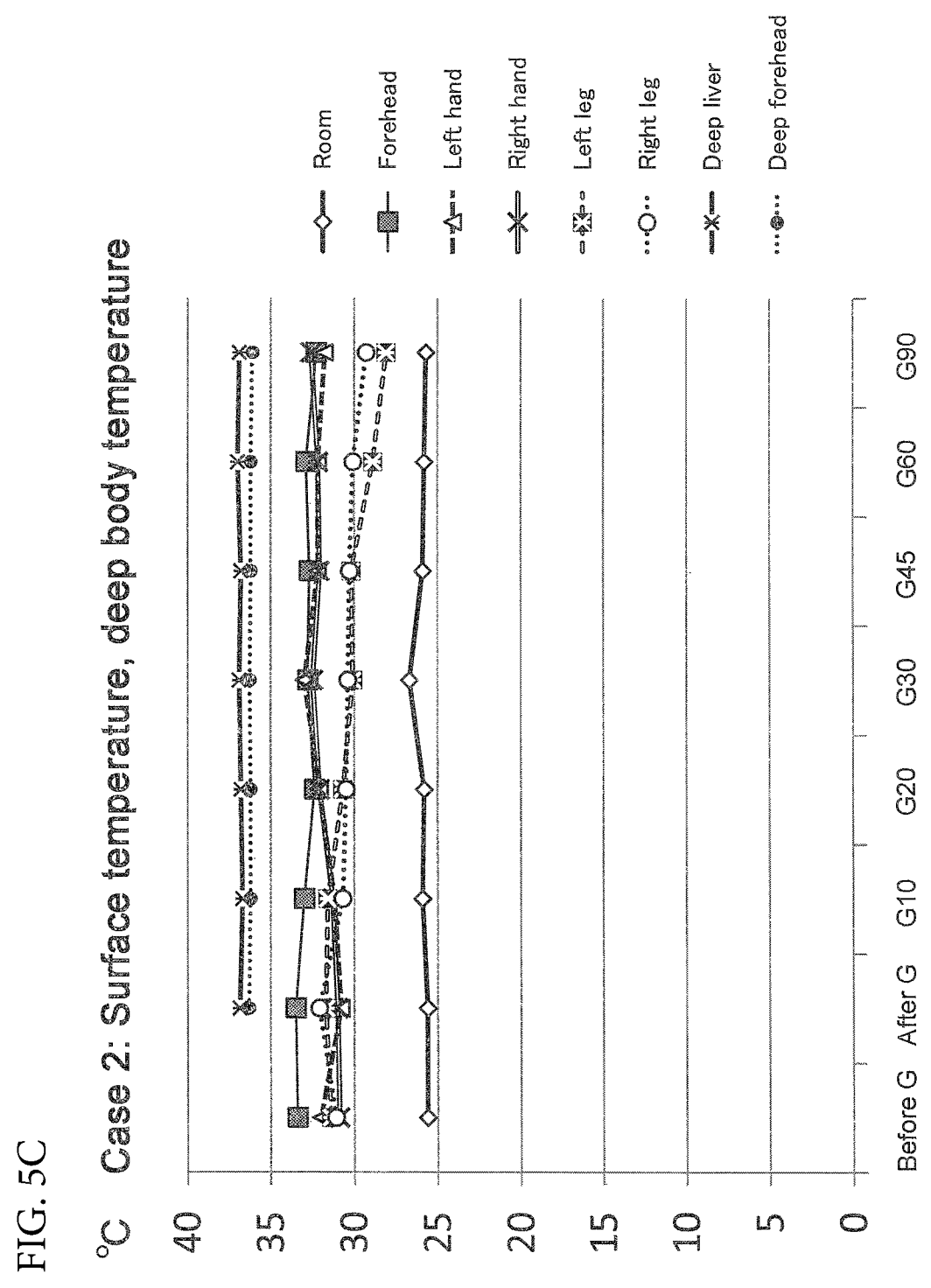

FIG. 5C shows time-dependent changes in surface temperature and deep body temperature in patients with RTT after administration of ghrelin.

FIG. 6 shows chest and abdominal movements in patients with RTT after administration of ghrelin.

FIG. 7 shows the results of a test investigating effects on breathing before and after intravenous administration of ghrelin in patients with RTT.

FIG. 8B shows the results of autonomic analysis (Holter electrocardiography) in patients with RTT after administration of ghrelin.

FIG. 9 shows that cortisol awaking response (CAR) was ameliorated by administration of ghrelin in patients with RTT.

FIG. 10 shows the results of melatonin measurements in the saliva of patients with RTT after administration of ghrelin.

FIG. 11 illustrates symptomatic progress in patients of interest with RTT, shown in the chronological order of symptom development.

FIG. 13 shows amelioration of dystonia by VAS in patients with RTT after administration of ghrelin.

BEST MODE FOR IMPLEMENTING THE INVENTION

Figure 1A:
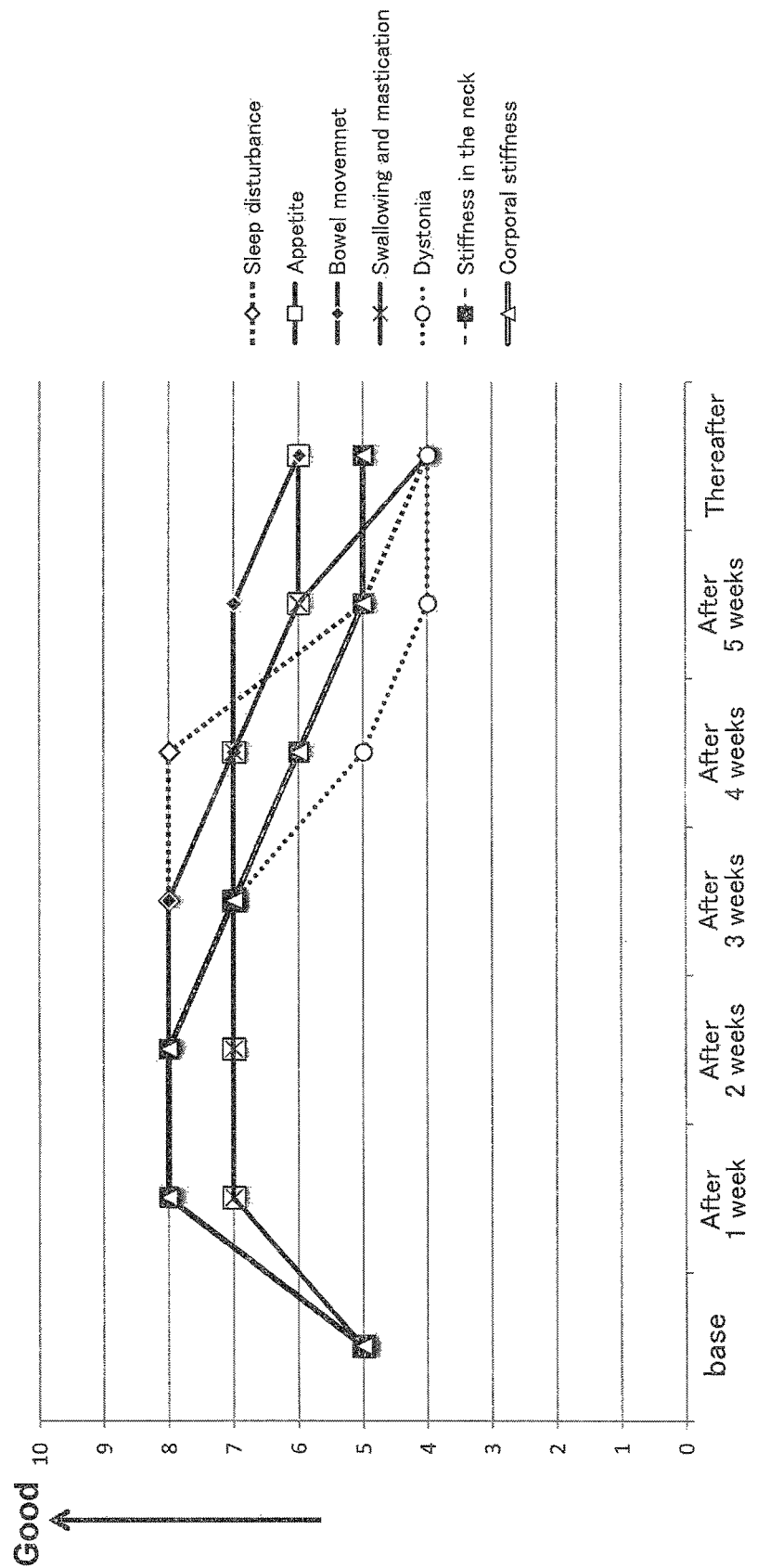
FIG. 1A shows amelioration of symptoms in patients with RTT after administration of ghrelin.

Currently, ghrelin is undergoing clinical testing for gastrointestinal symptoms such as anorexia nervosa and cardiovascular disorders and for use after total gastrectomy. These tests are performed without showing significant side effects. In accordance with the present invention, amelioration of eating disorders, constipation, autonomic symptoms and central nervous system manifestations—which impair quality of life of, and are involved in lifespan prognosis of, patients with RTT—is expected after ghrelin administration.

Ghrelin as used herein is active ghrelin showing its original physiological activities wherein the side chain of the 3rd amino acid residue in a peptide consisting of 28 amino acid residues is modified with octanoic acid. Ghrelin as used herein may be a ghrelin derivative where any one to several of the 28 amino acid residues is deleted, substituted or added, a ghrelin derivative substituted with lauric acid or palmitic acid in place of octanoic acid, a ghrelin derivative substituted with an unsaturated fatty acid or a branched fatty acid (e.g. 3-octenoyl (C8:1) or 4-methylpentanoyl) in place of octanoic acid, or a ghrelin derivative substituted with an aromatic amino acid, tryptophan, in place of octanoic acid, insofar as its physiological activity is maintained.

Ghrelin as used herein may be obtained by isolating the natural peptide or may be prepared in a conventional manner using a peptide synthesizer. A method for preparing ghrelin as used herein is not particularly limited. For instance, ghrelin as used herein may be prepared by isolation from ghrelin producing cells of the human gastric corpus or by a gene recombination technique. In case of isolation from ghrelin producing cells, ghrelin may be purified by chromatography. For instance, ghrelin may be purified by gel filtration, two ion exchange HPLCs, and reverse phase HPLC. Ghrelin as used herein may also be purified by affinity chromatography using a suitable carrier to which an antibody to ghrelin is bound.

After purification, ghrelin is dissolved in solvent and the solution is aseptically filtered and transferred to an ample or vial to prepare the composition of the present invention. For a solvent, distilled water for injection, saline, 0.01 M to 0.1 M phosphate buffer and the like may be used, if necessary, in admixture with ethanol, glycerol, etc. Furthermore, after ghrelin is dissolved in a solvent, the solution is aseptically filtered, transferred to an ample, a vial etc. and lyophilized to prepare the pharmaceutical composition of the present invention.

The therapeutic agent of the present invention may also be mixed with sugars such as mannitol, glucose and lactose, salts such as common salt and sodium phosphate, and the like, as additives. The pharmaceutical composition of the present invention in a dissolved state usually has a pH ranging from 6.8 to 7.5, preferably 7.3 to 7.4, more preferably 7.35.

The route of administration of the pharmaceutical composition of the present invention is not particularly limited and is in accordance with common practice including, for instance, oral administration, intraperitoneal injection, intratracheal injection, intrabronchial injection and direct intrabronchial instillation, subcutaneous injection, transdermal delivery, intra-arterial injection, intravenous injection, nasal administration and the like. However, it is preferably administered via parenteral administration, namely, subcutaneous, intradermal or intravenous injection. The pharmaceutical composition for parenteral administration includes a solution of ghrelin of the present invention dissolved in a commonly acceptable carrier, preferably an aqueous carrier. A variety of aqueous carriers, all known in the art, may be used, including, for instance, water, buffer, brine, glycine and the like. These solutions are sterilized and generally contain no particulate substances. These pharmaceutical compositions may be sterilized by a method for sterilization well known in the art. The composition of the present invention may be supplemented with a commonly used additive, for instance, a stabilizing agent (arginine, polysorbate 80, macrogol 4000, etc.), an excipient (mannitol, sorbitol, sucrose, etc.) and the like, and formulated for injection or in preparations that can be administered transmucosally (nasally, orally or sublingually) by procedures such as sterile filtration, dispersion, lyophilization, etc.

In accordance with the present invention, a therapeutically effective amount of ghrelin may vary depending on the severity of disease state, age, body weight etc. of the subject and is ultimately determined at the discretion of the physician. Normally, ghrelin may be administered once at a dose of 0.03 μg/kg/day to 10 μg/kg/day, preferably 1 μg/kg/day to 5 μg/kg/day, more preferably 1 μg/kg/day to 3 μg/kg/day. A dose of 3 μg/kg/day is the most preferable. A skilled person could determine the necessary procedural regimen, depending on the severity of a specific disease and condition to be treated, using a standard pharmacological method.

For assessment of RTT, four international scales, the Rett Syndrome Behavioral Questionnaire (RSBQ), the Anxiety Depression and Mood Scale (ADAMS), Burke-Fahn-Marsden Dystonia Rating Scale (BFMDRS) and Pittsburgh Sleep Quality Index (PSQI) for caregivers, and the Neurological Test Chart developed by the Japanese Society of Child Neurology are known. A visual analog scale (VAS) with 5 as the baseline, 10 as the best and 0 as the worst may be used by parents or physical therapists. In the present invention, dystonia was assessed using the international BFMDRS. The VAS assesses appetite, bowel movement, dystonia, vasomotor reflex, sleep, swallowing etc.

Test items evaluated in patients with RTT are the following: As test items, cortisol in saliva, ghrelin, growth hormone, IGF-1, blood glucose in blood etc. were measured in addition to breathing and cardiac function. Sleep was assessed with a sleep diary and by actigraphy. Day-long EEG video monitoring was also used for assessment, before and after ghrelin administration.

Breathing pattern: chest/abdominal sensor, $SpO_2$ monitor
Circulation: 12-lead electrocardiogram
Temperature: surface temperature, deep body temperature, thermography
Sleep: sleep diary, actigraphy
Blood test: ghrelin, growth hormone, blood glucose, IGF-1 etc.
Saliva: cortisol, melatonin, MHPG etc.
Electroencephalogram (EEG): 24-hour EEG video monitoring
Autonomic nervous system: Holter electrocardiography Ghrelin has a variety of physiological activities besides appetite promotion and GH secretion. It is known that ghrelin alleviates and modulates sympathetic hypertonic autonomic nerves and impaired autonomic nerve imbalances are observed in RTT. Patients with RTT having eating disorders exhibit significantly lower levels of both total ghrelin and active ghrelin than do controls. Lower total ghrelin levels are significantly correlated with constipation. RTT model animals have lower brain weights than control animals, with microcephalic tendencies and also have lower plasma ghrelin levels.

The present invention is explained in more detail in the following examples but is not limited thereto.

Example 1

After approval of the ethics committee of Kurume University, the test was conducted after obtaining Informed Consent (IC) from the patients' parents. Four patients aged 21 years old (case 1), 12 years old (case 2), 22 years old (case 3) and 32 years old (case 4), each with the MECP2 mutation and a definitive diagnosis, were subjected to the test (Table 1). Ghrelin was intravenously administered in the morning, after fasting for 3 days. For clinical data, RTT Behavioral Questionnaire, Burke-Fahn-Marsden Dystonia Rating Scale, VAS (Visual Analog Scale; 5: baseline before treatment; 10: markedly improved; 0: markedly worsened) evaluated by their parents, and a sleep diary were used. For biochemical data, plasma levels of ghrelin, GH, blood glucose, saliva cortisol and melatonin were obtained. For physiological data, electroencephalogram, respiration sensor, Holter electrocardiography and actigraphy were used.

TABLE 1

List of backgrounds of patients with ghrelin administration

| Case: Age | Case1: 21 years old | Case2: 12 years old | Case3: 22 years old | Case4: 32 years old |
| --- | --- | --- | --- | --- |
| Genetic mutation | c.C476T | c.G232A | c.C883T | c.1196_1200delCCACC |
| ADL | Bedridden | Able to roll over | Bedridden | Able to walk alone |
| Sleep disturbance | Yes | None | Yes | Yes |
| Epilepsy | None | Yes | Yes | Yes |
| Hyperventilation/Apnea | None | Yes | Yes | None |
| Abnormal electro cardiogram | Mild long QT | VPC | None | None |
| Dystonia | Yes | Yes | Yes | Yes |
| Scoliosis | Yes | None | Yes | Yes |
| Alimentation | Oral + Gastrostomy | Oral | Oral | Oral |
| Bowel movement | Diarrhea after gastrostomy | Constipation | Constipation | Constipation |
| Medication | CBZ, VPA, CLB, LEV Pramipexole Piperidone Alfacalcidol Calcium lactate | CBZ, VPA, CLB Magnesium oxide | CBZ, VPA, CLB Aripiprazole Melatonin Magnesium oxide | Flunitrazepam Eperisone Magnesium oxide Sennoside Ramelteon Suvorexant |

The protocol for the study was as follows:
On the 1st day in the hospital: wear actigraphy sensor (return it on leaving the hospital), saliva sampled every 3 hours after 12 o'clock.
In the hospital (ghrelin administration once daily, in the morning):
In the morning without breakfast
Intravenous line (saline with heparin lock) inserted before breakfast
Administration of ghrelin (3 µg/kg/day), at 9 a.m. for 3 consecutive days
After administration, allowed to eat normally Ghrelin blood sampling: before, immediately after, 30 minutes after and 60 minutes after ghrelin administration GH blood sampling: before, immediately after, 30 minutes after, 60 minutes after and 90 minutes after ghrelin administration
Saliva sampling: at bedtime of the 1st day in the hospital and immediately after awakening on the 2nd day, thereafter every 3 hours until bedtime
Assessment: neurological examination on admission to the hospital
Central nervous system: seizure frequency, dystonia
Neurological Test Chart check, etc.
Autonomic nervous system: Holter electrocardiography: RR interval, sympathetic thermography, deep body temperature measurement
Others: constipation status, duration of eating (mean duration of eating time in the morning, afternoon and evening), sleep, respiratory abnormalities, scoliosis, grinding of the teeth, developmental psychomotor milestones, and other clinical parameters The patients were admitted to the hospital in the morning after their histories were taken, wore actigraphy devices until dinner, and had saliva sampled with cotton swabs and sample tube for collecting and storing samples. Fasting before breakfast, venous line maintained with saline (with heparin lock) was inserted and ghrelin was administered at 3 µg/kg/day. Blood sampling for ghrelin and growth hormone (GH) measurements was performed and saliva was successively sampled to measure cortisol, neurotransmitter and the like. Ghrelin was administered before breakfast on 3 consecutive days, a total of 3 administrations. The amount of blood sampled for ghrelin measurements was 2 ml each, a total of 8 ml, and sampling was done before, immediately after, 30 minutes after and 60 minutes after administration of ghrelin, a total of 4 times. GH sampling was conducted a total of 5 times on the first day in the hospital. The amount of blood collected for GH measurements was 0.5 ml whole blood per sampling, a total of 2.5 ml, and blood samples were collected once between 9:00 and 9:30 a.m. before the initiation of the test, and immediately after, 30 minutes after, 60 minutes after and 90 minutes after ghrelin administration, a total of 5 times. Saliva samples were collected 30 minutes after awakening and then 3 hours later before bedtime at 21 o'clock in the evening. The amount of each saliva sample was approximately 500 µl. On the day of release from the hospital, the short-term effects of ghrelin were assessed and each patient was informed of the next appointment day.

Figure 1B:
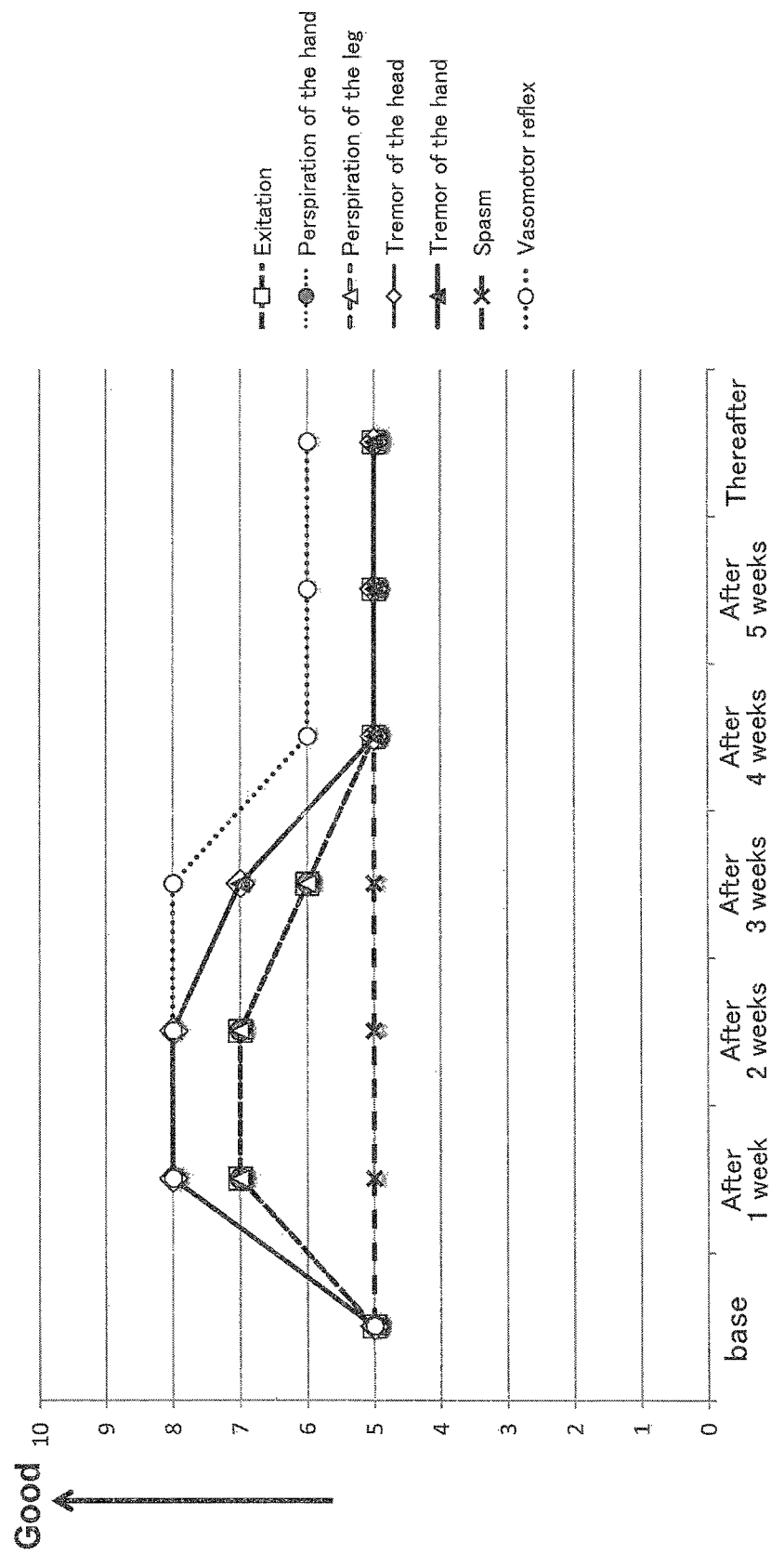
FIG. 1B shows amelioration of symptoms in patients with RTT after administration of ghrelin.
Figure 1C:
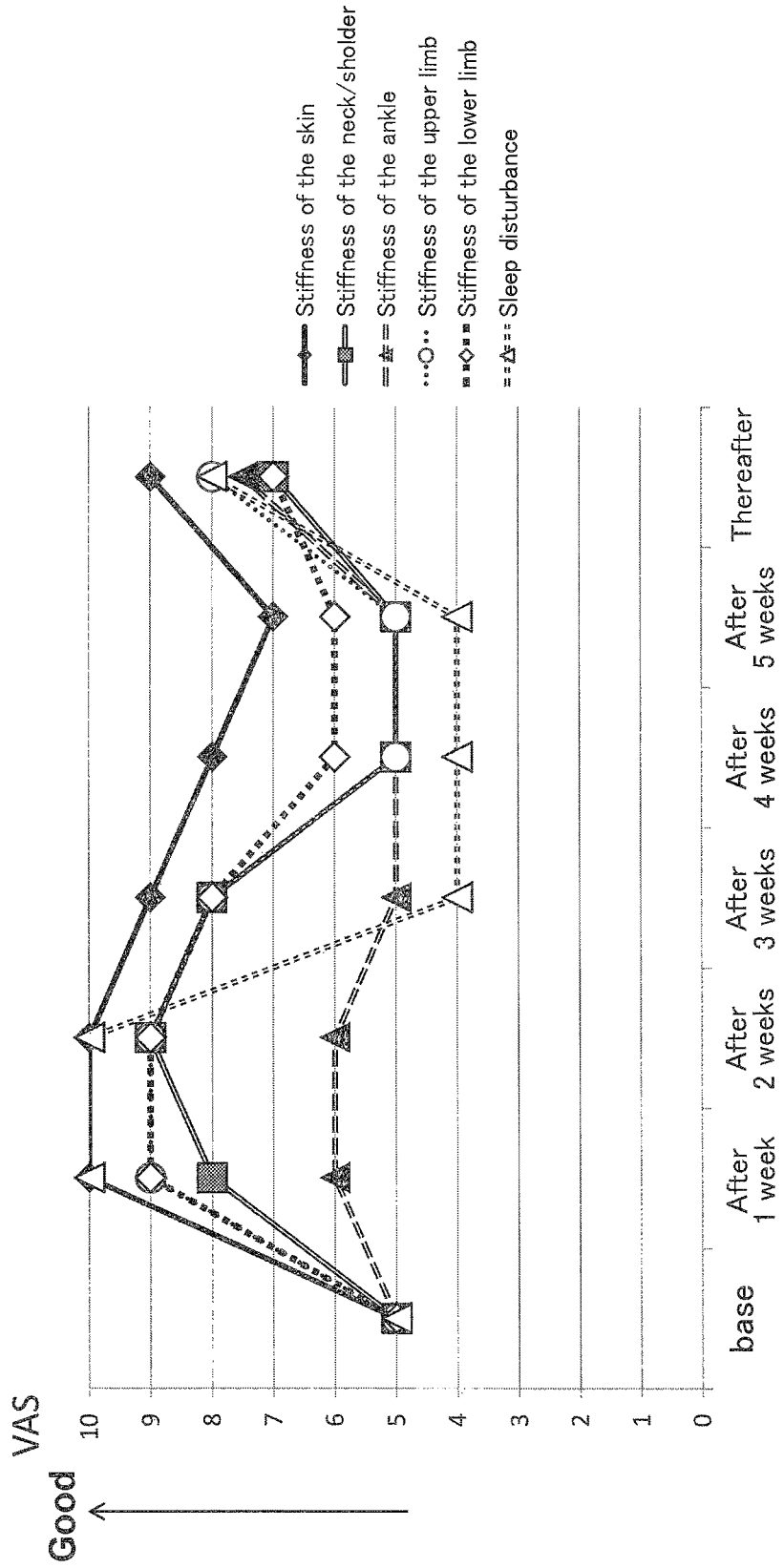
FIG. 1C shows amelioration of symptoms in patients with RTT after administration of ghrelin.

In the 21 year old female (case 1), dystonia and sleep disturbances were markedly alleviated and melatonin, which has been taken orally in a large amount for a long time, could be discontinued (FIGS. 1-1 and 1-2), provided that, about 3 weeks after ghrelin administration, the symptoms had returned to those before the treatment. Improved conditions were maintained after consecutive administration of ghrelin for 2 days every 3 weeks and alleviation of the symptoms continued for about 1 year without side effects. In the 32 year old female (case 4), dystonia and sleep disturbances were markedly alleviated and improved conditions were maintained after consecutive ghrelin administration for 2 days every 3 weeks and the alleviation of symptoms continued for about 4 months without side effects (FIG. 1-3).

Figure 5A:
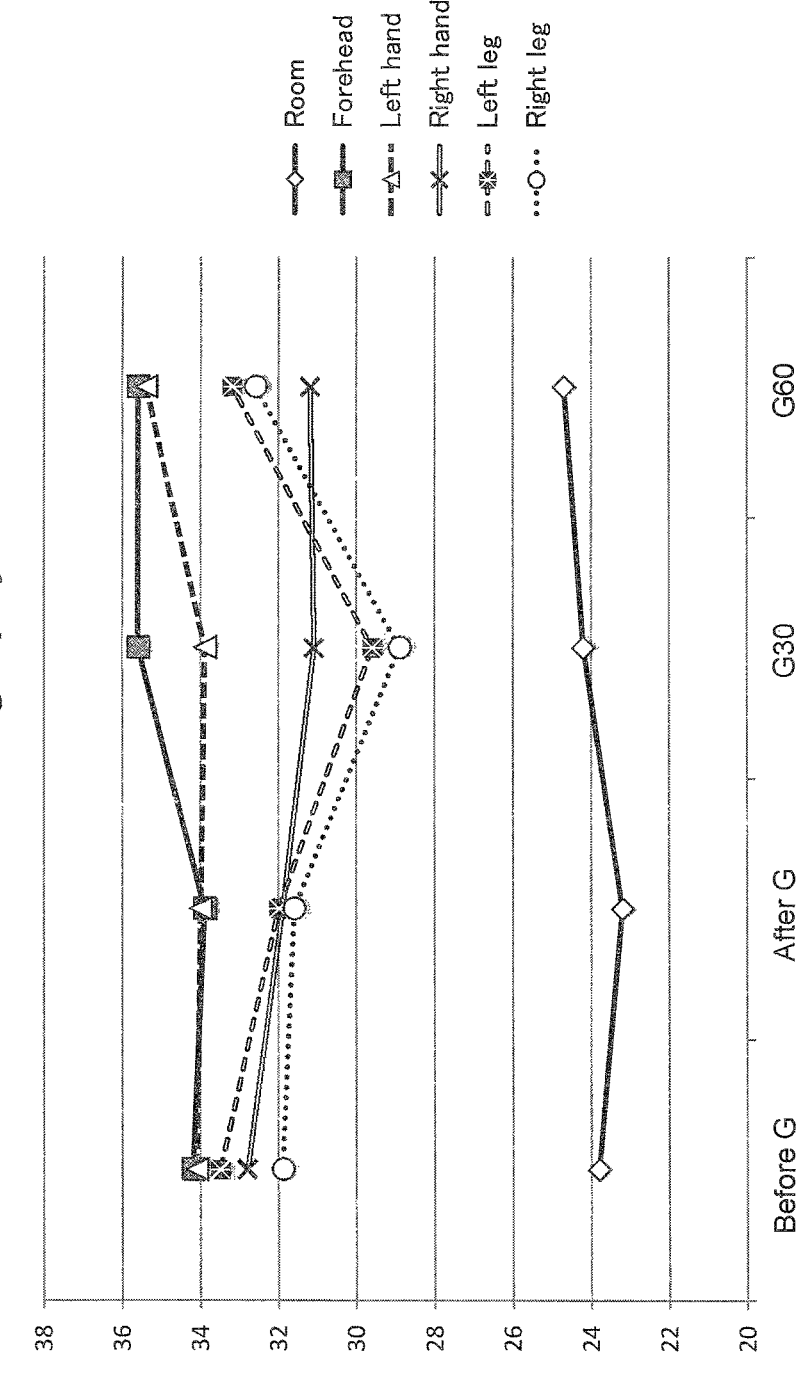
FIG. 5A shows time-dependent changes in thermography in patients with RTT after administration of ghrelin.
Figure 5B:
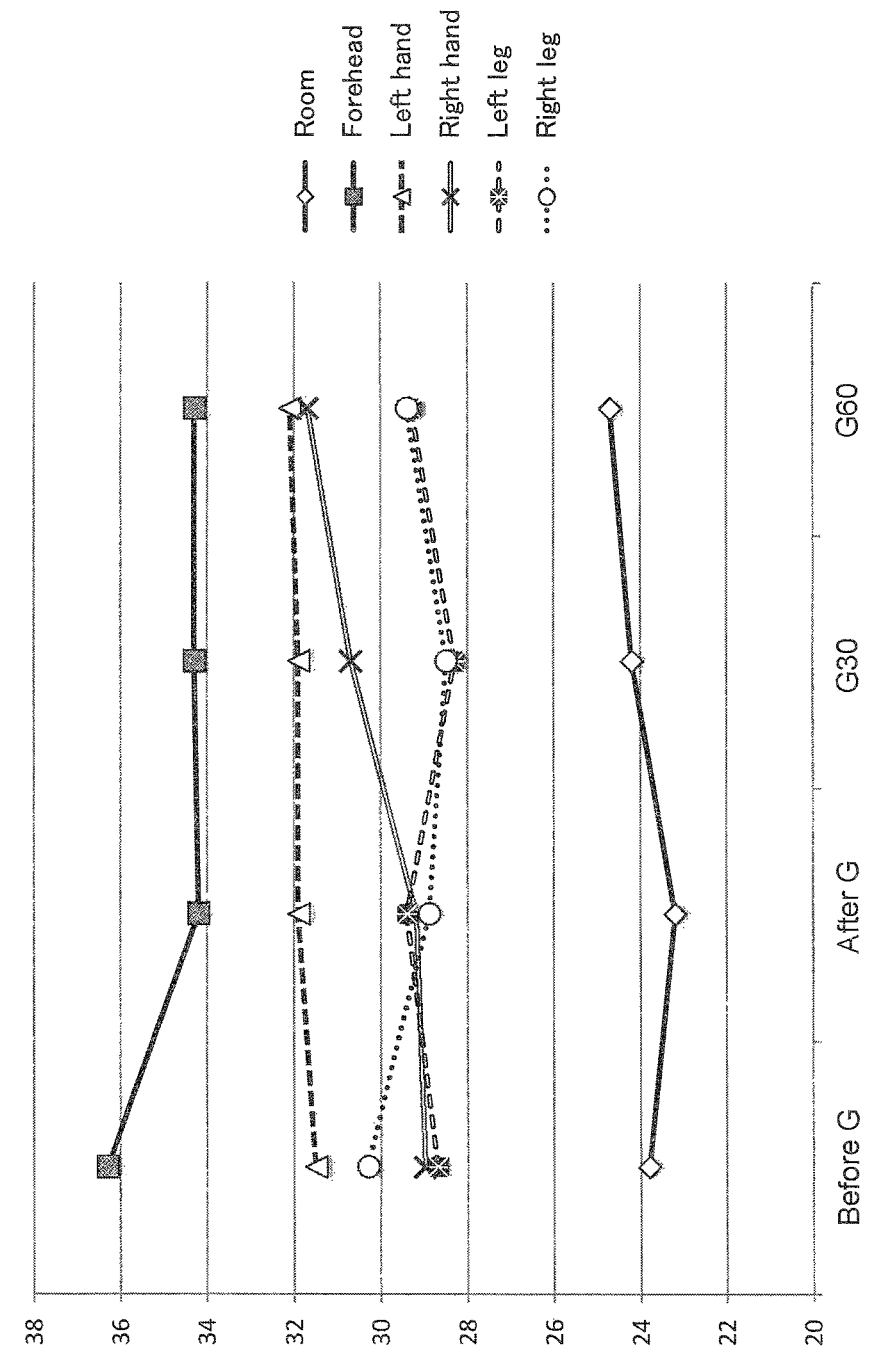
FIG. 5B shows time-dependent changes in surface temperature in patients with RTT after administration of ghrelin.
Figure 8A:
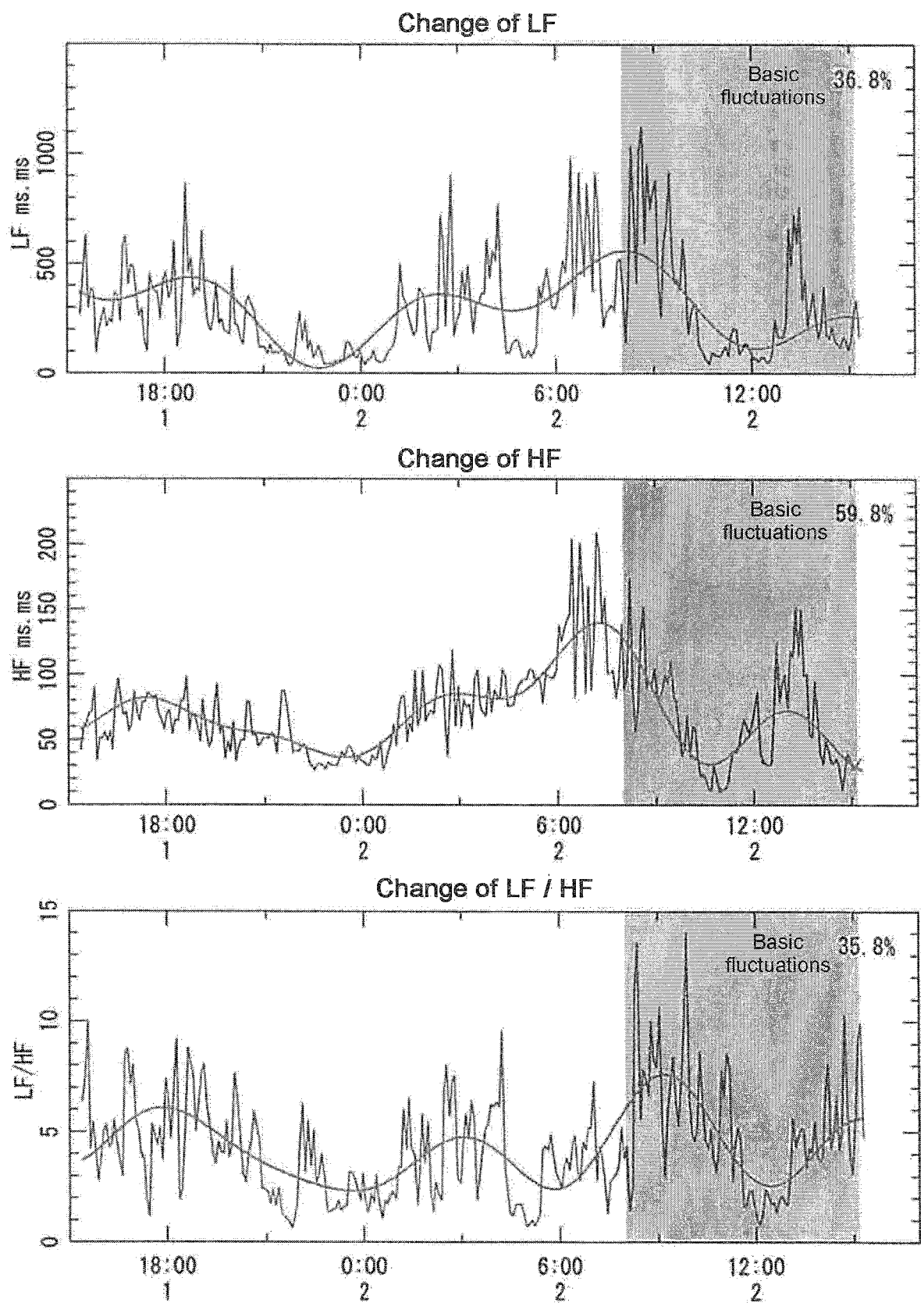
FIG. 8A shows the results of autonomic analysis (Holter electrocardiography) in patients with RTT after administration of ghrelin.
Figure 12A:
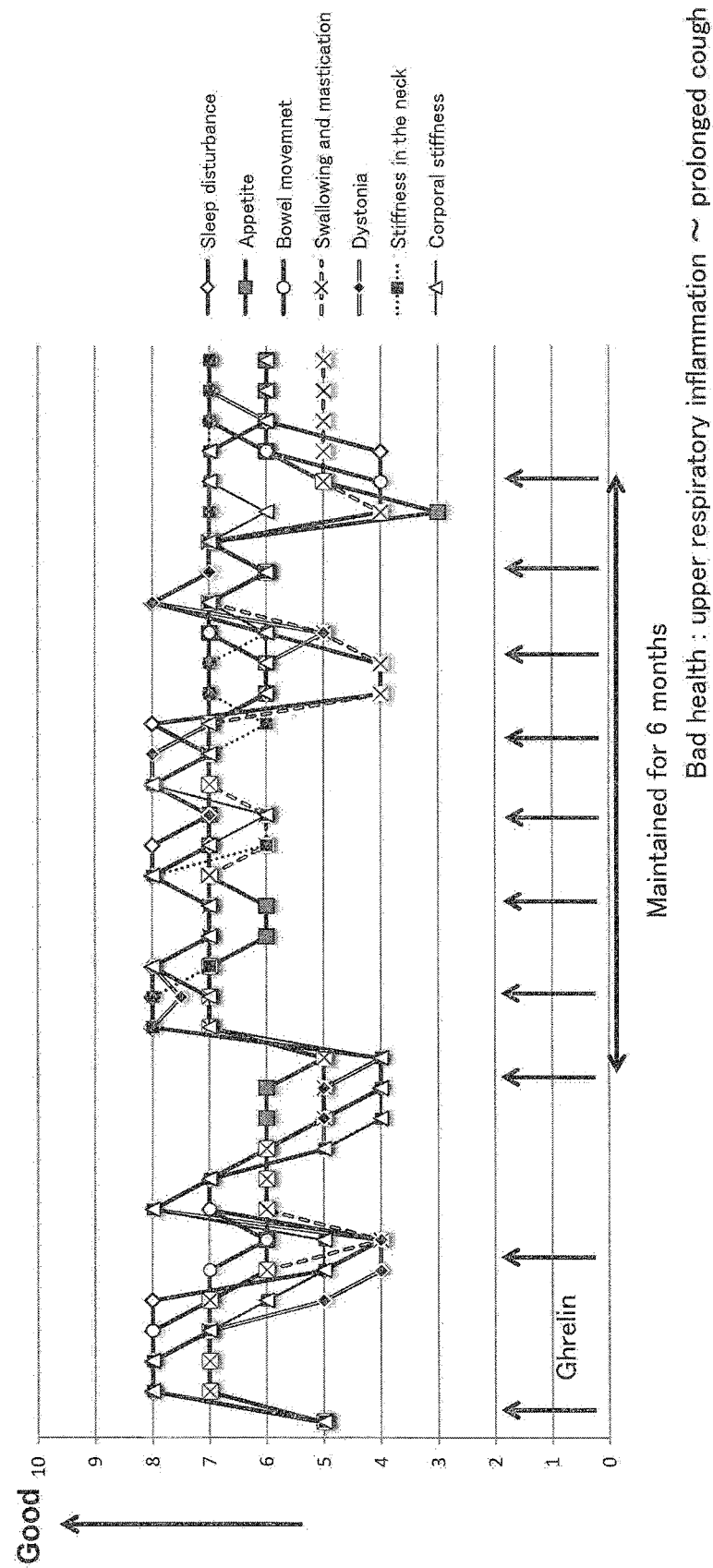
FIG. 12A shows time-dependent changes in VAS in patients with RTT after administration of ghrelin.
Figure 12B:
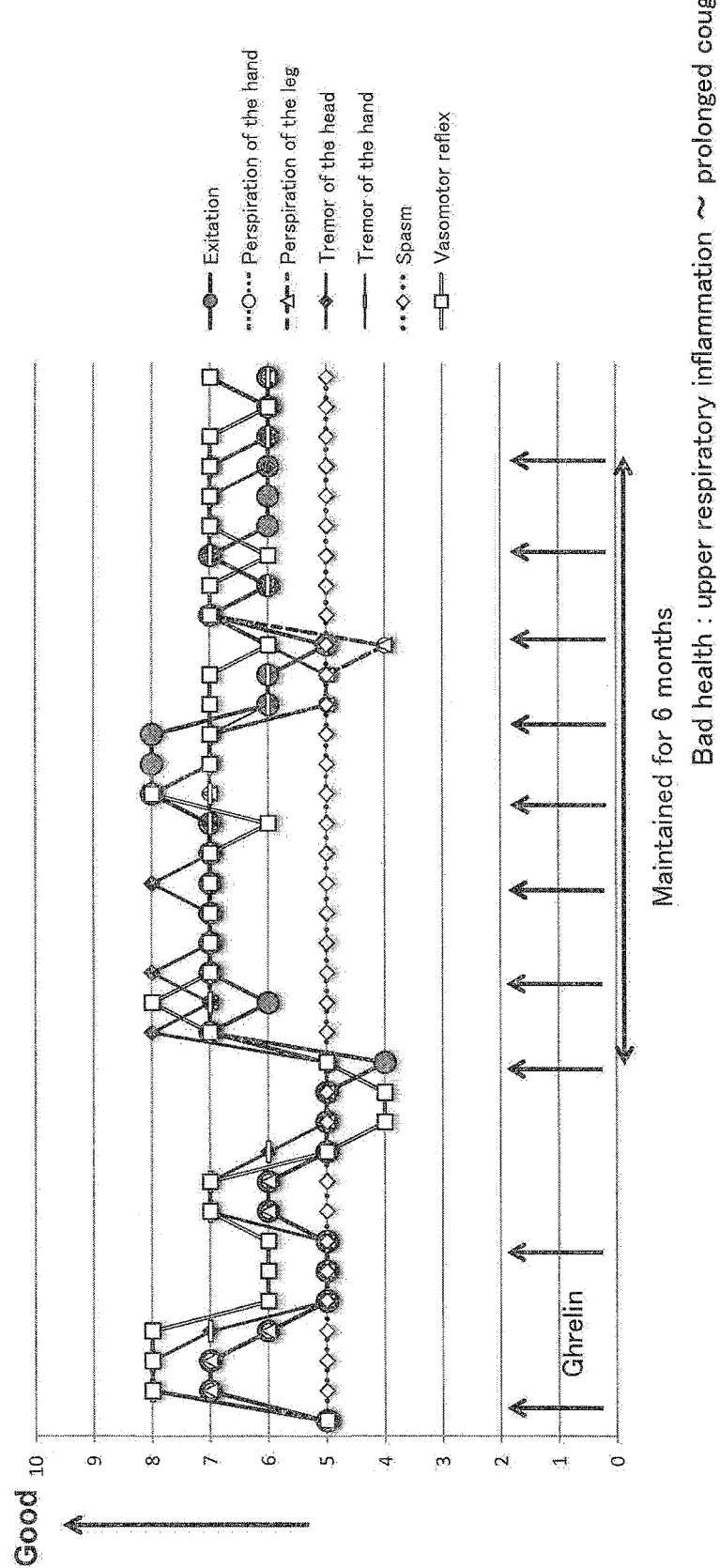
FIG. 12B shows time-dependent changes in VAS in patients with RTT after administration of ghrelin.
Figure 14A:
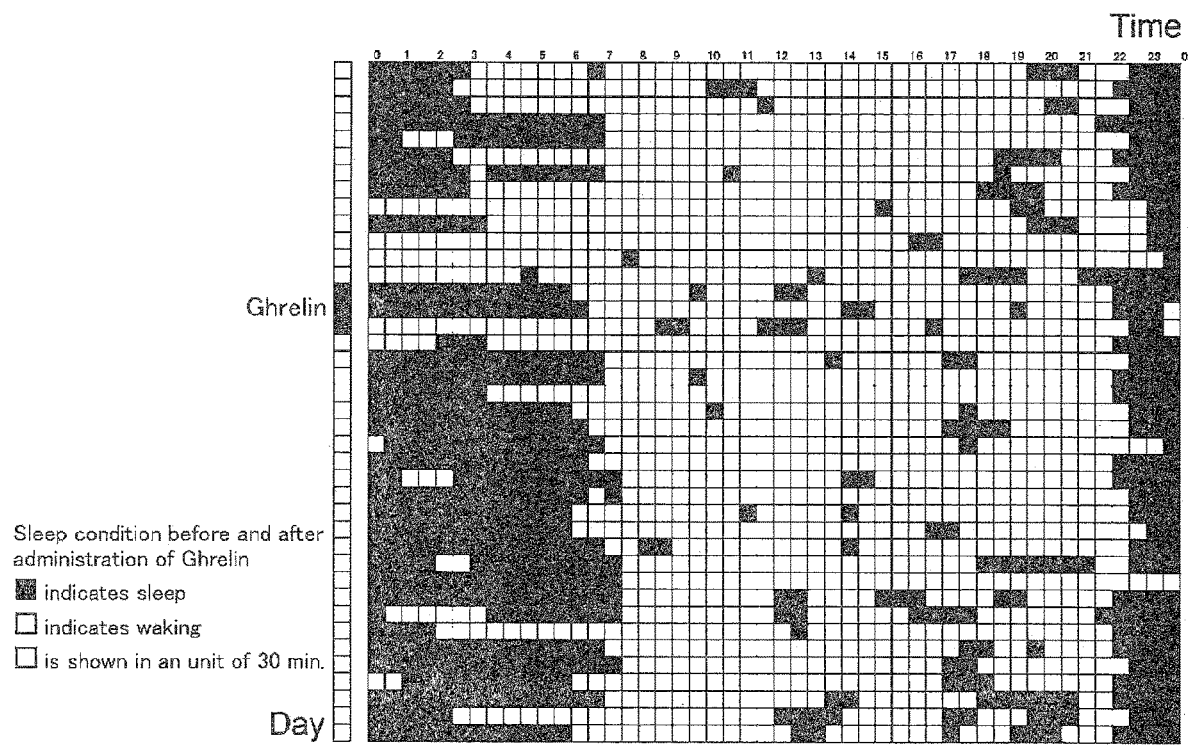
FIG. 14A shows the sleep diary of a patient (Case 1) with RTT before and after administration of ghrelin.
Figure 14B:
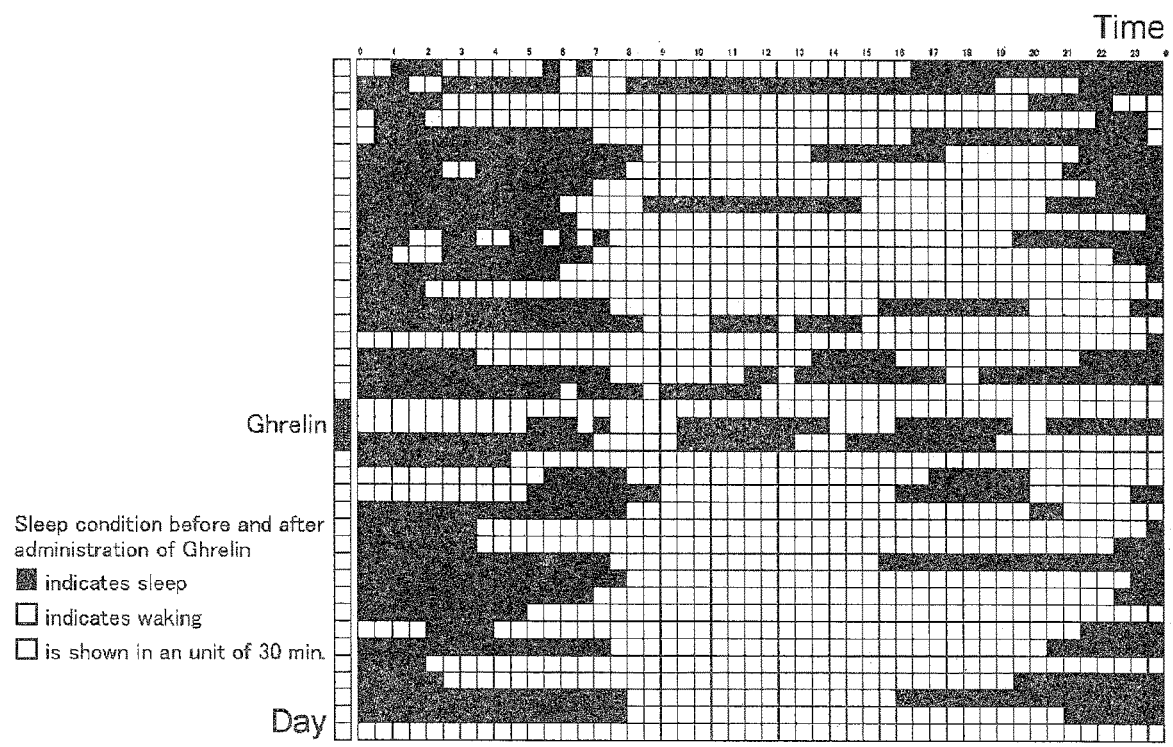
FIG. 14B shows the sleep diary of a patient (Case 4) with RTT before and after administration of ghrelin.

The plasma ghrelin levels increased immediately after administration and returned to baseline levels after about 60 minutes (FIG. 2). GH levels reached a peak of secretion (30 to 175 times higher than baseline level) at 30 minutes after ghrelin administration (G in the figure) at 3 µg/kg (FIG. 3). Blood glucose levels increased slightly at 30 to 60 minutes after ghrelin administration (FIG. 4). Ghrelin administration did not affect surface temperature or deep body temperature (FIG. 5). The temperature tended to once decrease and then increase. It was difficult to keep environmental conditions constant, such as room temperature, clothes and bed/couch, making these temperature assessments difficult. Most of the patients with RTT showed respiratory abnormalities such as hyperventilation and/or apnea. There were no significant changes in breathing or chest movements after ghrelin administration (FIGS. 6 and 7). Breathing was monitored in the waking state and compared before and after intravenous ghrelin administration. Apnea for 10 seconds or more, its frequency and total time, hypopnea for 10 seconds or less, its frequency and total time, were assessed but no significant effects on breathing abnormalities were observed. The results of autonomic analysis (Holter electrocardiography) are shown in FIG. 8. Cortisol awaking response (CAR), reflecting awaking rhythm and the autonomic nerves, is seen in healthy adults at 30 minutes after awakening and is regarded as an important reaction predominantly of the sympathetic nervous system. CAR was not observed in the patients with RTT (FIG. 9). After ghrelin administration, these CAR deficits appeared to be alleviated. The results of saliva melatonin measurements are shown in FIG. 10. Ghrelin administration induced peaks of melatonin. FIG. 11 illustrates symptomatic progress in one of the patients. Time-dependent changes in VAS and amelioration of dystonia by VAS are shown in FIGS. 12-1 and 12-2 and FIG. 13, respectively. A sleep diary before and after ghrelin administration is shown in FIG. 14. Improvement of sleep rhythms was reported in the sleep diary.

After the therapy in accordance with the present invention, the mother of the 21 year old female patient made the following remarks: "she became calm and peaceful; I'm glad that she looks merry; she got to be able to sleep, no longer needs melatonin, and more active during the day; her duration of eating became shorter; she got to have formed stool (I was afraid of worsening of diarrhea); dystonia was ameliorated; she got to be able to open the mouth at the dental checkup; PT was surprised; tremor of the head decreased and hair sprouted; vasomotor nerve reflex was ameliorated (frequency became lowered, time was reduced by half (from 20 minutes to 10 minutes), she got no longer sweaty)." In the 32-year-old female, dystonia was ameliorated, it became easier for her to open her mouth and she became able to eat large amounts of solid foods. Hypertonia of the cheeks and around the mouth, shoulder and abdomen was ameliorated. Sleep was also improved. She had difficulty sleeping before treatment even with two tablets of suvorexant and two tablets of ramelteon and, thus, had also taken 5 mg of diazepam. After treatment, she became able to sleep with only one tablet each of suvorexant and ramelteon and the number of days when a hypnotic agent was also required were decreased by half.

INDUSTRIAL APPLICABILITY

The prophylactic and therapeutic agent for RTT of the present invention comprising a therapeutically effective amount of ghrelin can be administered to patients safely without severe side effects and can be used effectively for therapy of RTT, such as increasing GH secretion and ameliorating constipation, sleep, muscle tone and dystonia.

The invention claimed is:

1. A method of treating Rett Syndrome (RTT) comprising intravenously administering ghrelin to a subject in need thereof in an amount of 3 micrograms/kg/day for three consecutive days, and repeated every three weeks thereafter for two consecutive days.

2. The method of claim 1, wherein the side chain of serine at the 3rd position of ghrelin is modified with octanoic acid.

* * * * *

SEQUENCE LISTING

<160> NUMBER OF SEQ ID NOS: 1

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25